US009706976B2

(12) United States Patent
Randall et al.

(10) Patent No.: US 9,706,976 B2
(45) Date of Patent: Jul. 18, 2017

(54) ULTRASOUND IMAGING SYSTEMS AND METHODS OF PERFORMING ULTRASOUND PROCEDURES

(75) Inventors: Kevin S. Randall, Ambler, PA (US); Joseph A. Urbano, Audubon, PA (US); Lawrence A. Engle, Stowe, PA (US)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 648 days.

(21) Appl. No.: 11/672,622

(22) Filed: Feb. 8, 2007

(65) Prior Publication Data
US 2008/0194964 A1   Aug. 14, 2008

(51) Int. Cl.
A61B 8/00   (2006.01)

(52) U.S. Cl.
CPC .............. *A61B 8/00* (2013.01); *A61B 8/4405* (2013.01); *A61B 8/4411* (2013.01); *A61B 8/4455* (2013.01); *A61B 8/4472* (2013.01); *A61B 8/56* (2013.01); *A61B 2562/222* (2013.01)

(58) Field of Classification Search
USPC .................... 600/437, 459; 382/128; 73/625; 439/271
See application file for complete search history.

(56) References Cited

U.S. PATENT DOCUMENTS

| 4,140,022 | A |   | 2/1979  | Maslak          | 73/626     |
|-----------|---|---|---------|-----------------|------------|
| 4,246,792 | A |   | 1/1981  | Matzuk          | 73/620     |
| 4,413,629 | A |   | 11/1983 | Durley, III     | 128/660    |
| 4,604,697 | A |   | 8/1986  | Luthra et al.   | 364/414    |
| 4,691,157 | A |   | 9/1987  | McDermott       |            |
| 4,853,904 | A |   | 8/1989  | Pesque          | 367/89     |
| 5,014,712 | A |   | 5/1991  | O'Donnell       | 128/661.01 |
| 5,070,881 | A | * | 12/1991 | Weiland         | 600/459    |
| 5,165,415 | A | * | 11/1992 | Wallace et al.  | 600/452    |
| 5,229,933 | A |   | 7/1993  | Larson, III     | 364/413.25 |
| 5,247,524 | A |   | 9/1993  | Callon          | 371/53     |
| 5,278,757 | A |   | 1/1994  | Hoctor et al.   | 364/413.25 |
| 5,295,485 | A | * | 3/1994  | Shinomura et al.| 600/443    |
| 5,477,858 | A |   | 12/1995 | Norris et al.   |            |
| 5,520,187 | A |   | 5/1996  | Snyder          | 128/661.01 |
| 5,544,654 | A |   | 8/1996  | Murphy          | 128/660.07 |
| 5,590,658 | A |   | 1/1997  | Chiang et al.   | 128/661.01 |
| 5,640,960 | A |   | 6/1997  | Jones et al.    | 128/661.07 |

(Continued)

FOREIGN PATENT DOCUMENTS

EP   0 762 142 B1   3/1997

OTHER PUBLICATIONS

U.S. Appl. No. 11/595,340, filed Nov. 10, 2006, Urbano et al.

(Continued)

*Primary Examiner* — Joseph M Santos Rodriguez

(57) ABSTRACT

Ultrasound imaging systems can include a probe, and a cable that can be removably connected to the probe. The probes for ultrasound imaging systems may include a transducer array that emits acoustical energy and receives return reflections of the acoustical energy, a circuit board, a transmitter mounted on the circuit board and communicatively coupled to the transducer array for transmitting information relating to the return reflections, and a housing. The housing has an interior volume and the transducer array, the circuit board, and the transmitter are positioned in the interior volume. A battery pack may be removably mounted to the housing. The battery pack may provide electrical power for the transducer array.

40 Claims, 16 Drawing Sheets

(56) References Cited

U.S. PATENT DOCUMENTS

| | | | |
|---|---|---|---|
| 5,685,307 A | 11/1997 | Holland et al. | 128/660.01 |
| 5,690,114 A | 11/1997 | Chiang et al. | 128/661.01 |
| 5,713,363 A | 2/1998 | Seward et al. | 128/662.06 |
| 5,722,412 A | 3/1998 | Pflugrath et al. | 128/662.03 |
| 5,738,099 A | 4/1998 | Chang | 128/662.03 |
| 5,774,499 A | 6/1998 | Ahn et al. | 375/261 |
| 5,817,024 A | 10/1998 | Ogle et al. | 600/447 |
| 5,839,442 A | 11/1998 | Chiang et al. | 128/661.01 |
| 5,846,205 A | 12/1998 | Curley et al. | 600/472 |
| 5,865,733 A | 2/1999 | Malinouskas et al. | 600/300 |
| 5,893,363 A | 4/1999 | Little et al. | 600/447 |
| 5,921,932 A | 7/1999 | Wright et al. | 600/447 |
| 5,951,479 A | 9/1999 | Holm et al. | 600/447 |
| 5,957,846 A | 9/1999 | Chiang et al. | 600/447 |
| 5,964,709 A | 10/1999 | Chiang et al. | 600/447 |
| 6,007,490 A * | 12/1999 | Pawluskiewicz | 600/459 |
| 6,029,116 A | 2/2000 | Wright et al. | 702/32 |
| 6,102,863 A | 8/2000 | Pflugrath et al. | 600/447 |
| 6,113,547 A | 9/2000 | Catallo et al. | 600/459 |
| 6,117,085 A * | 9/2000 | Picatti et al. | 600/459 |
| 6,135,961 A | 10/2000 | Pflugrath et al. | 600/447 |
| 6,139,496 A * | 10/2000 | Chen et al. | 600/437 |
| 6,142,946 A | 11/2000 | Hwang et al. | 600/459 |
| 6,148,224 A | 11/2000 | Jensen | 600/407 |
| 6,174,286 B1 | 1/2001 | Ramamurthy et al. | 600/447 |
| 6,230,000 B1 | 5/2001 | Tayloe | 455/323 |
| 6,251,073 B1 | 6/2001 | Imran et al. | 600/443 |
| 6,251,078 B1* | 6/2001 | Moore et al. | 600/459 |
| 6,364,839 B1 | 4/2002 | Little et al. | 600/459 |
| 6,436,047 B1 | 8/2002 | Ramamurthy et al. | 600/447 |
| 6,450,958 B1 | 9/2002 | Linkhart et al. | 600/437 |
| 6,471,651 B1 | 10/2002 | Hwang et al. | 600/459 |
| 6,491,634 B1 | 12/2002 | Leavitt et al. | 600/447 |
| 6,497,664 B1 | 12/2002 | Randall et al. | 600/447 |
| 6,508,763 B1 | 1/2003 | Urbano et al. | 600/437 |
| 6,514,201 B1 | 2/2003 | Greenberg | 600/437 |
| 6,527,719 B1 | 3/2003 | Olsson et al. | 600/443 |
| 6,527,721 B1 | 3/2003 | Wittrock et al. | 600/446 |
| 6,569,102 B2 | 5/2003 | Imran et al. | 600/459 |
| 6,679,847 B1 | 1/2004 | Robinson et al. | 600/447 |
| 6,689,063 B1 | 2/2004 | Jensen et al. | 600/443 |
| 6,695,783 B2 | 2/2004 | Henderson et al. | 600/443 |
| 6,725,076 B1 | 4/2004 | Jensen | 600/407 |
| 6,743,175 B2 | 6/2004 | Greenberg | 600/437 |
| 6,780,154 B2 | 8/2004 | Hunt et al. | 600/446 |
| 6,859,659 B1 | 2/2005 | Jensen | 600/407 |
| 6,860,854 B2 | 3/2005 | Robinson | 600/447 |
| 7,052,459 B2 | 5/2006 | Washburn et al. | 600/437 |
| 2002/0107538 A1 | 8/2002 | Shibata et al. | |
| 2003/0085621 A1* | 5/2003 | Potega | 307/18 |
| 2004/0015079 A1* | 1/2004 | Berger et al. | 600/437 |
| 2004/0039254 A1* | 2/2004 | Stivoric | A61B 5/0205 600/300 |
| 2004/0068188 A1 | 4/2004 | Robinson | 600/447 |
| 2004/0111029 A1* | 6/2004 | Bates et al. | 600/437 |
| 2004/0181154 A1 | 9/2004 | Peterson et al. | 600/459 |
| 2004/0225220 A1 | 11/2004 | Rich | 600/446 |
| 2005/0043622 A1 | 2/2005 | Jensen | 600/449 |
| 2005/0054922 A1 | 3/2005 | Yudkovitch et al. | 600/437 |
| 2005/0131700 A1 | 6/2005 | Washburn et al. | 704/270 |
| 2005/0154304 A1 | 7/2005 | Robinson | 600/443 |
| 2005/0245132 A1 | 11/2005 | Huang et al. | |
| 2006/0017235 A1 | 1/2006 | Vesa | |
| 2006/0058655 A1 | 3/2006 | Little | 600/437 |
| 2006/0095045 A1* | 5/2006 | Trieu | 606/99 |
| 2006/0229598 A1 | 10/2006 | Shadduck | |
| 2006/0261778 A1* | 11/2006 | Elizalde Rodarte | 320/114 |
| 2007/0016058 A1 | 1/2007 | Kerwin | |
| 2007/0123797 A1* | 5/2007 | Krause | 600/562 |

OTHER PUBLICATIONS

U.S. Appl. No. 11/595,171, filed Nov. 10, 2006, Urbano et al.
U.S. Appl. No. 11/595,729, filed Nov. 10, 2006, Randall et al.
U.S. Appl. No. 11/595,027, filed Nov. 10, 2006, Urbano et al.
U.S. Appl. No. 11/595,033, filed Nov. 10, 2006, Klessel et al.
U.S. Appl. No. 11/595,706, filed Nov. 10, 2006, Weymer et al.
U.S. Appl. No. 11/595,164, filed Nov. 10, 2006, Randall et al.
U.S. Appl. No. 11/595,674, filed Nov. 10, 2006, Randall et al.
U.S. Appl. No. 11/595,335, filed Nov. 10, 2006, Randall et al.
U.S. Appl. No. 11/595,025, filed Nov. 10, 2006, Randall et al.
U.S. Appl. No. 11/595,601, filed Nov. 10, 2006, Urbano et al.
U.S. Appl. No. 11/595,341, filed Nov. 10, 2006, Randall, et al.
U.S. Appl. No. 11/595,701, filed Nov. 10, 2006, Urbano et al.
U.S. Appl. No. 11/595,334, filed Nov. 10, 2006, Urbano, et al.
U.S. Appl. No. 11/595,728, filed Nov. 10, 2006, Randall et al.
U.S. Appl. No. 11/595,557, filed Nov. 10, 2006, Randall, et al.
Bae, M.-H., et al., "Bidirectional pixel based focusing in conventional B-mode ultrasound imaging," Electronic Letters, Oct. 29, 1998, 34(22), 2105-2107.
Bae, M. H. et al., "Grating Lobe Reduction in Ultrasonic Synthetic Focusing," *Electronics Letters*, Jul. 4, 1991, 27(14), 1225-1227.
Bonnefous, O. et al., "Time Domain Formulations of Pulse-Doppler Ultrasound and Blood Velocity Estimation by Cross Correlation," *Ultrasonic Imaging*, 1986, 8, 73-85.
Chang, S. H. et al., "Phase-Error-Free Quadrature Sampling Technique in the Ultrasonic B-Scan Imaging System and Its Application to the Synthetic Focusing System," *IEEE Transacations on Ultrasonics, Ferroelectrics, and Frequency Control*, May 1993, 40(3), 216-223.
Cho, W-H. et al., "Multi-Order Sampling for Digital Beamforming of Wide-Band Signals," *IEEE Transactions on Ultrasonics, Ferroelectrics, and Frequency Control*, May 1996, 43(3), 495-499.
Coldani, G., et al., "An Instrument to Measure Velocity Profile by Means of Ultasound Techniques," *Journal of Mechanics in Medicine and Biology*, 2003, 3(1), 21-30.
Flax, S. W. et al., "Phase-Aberration Correction Using Signals From Point Reflectors and Diffuse Scatterers: Basic Principles," *IEEE Transactions on Ultrasonics, Ferroelectrics, and Frequency Control*, Nov. 1988, 35(6), 758-767.
Jensen, J. A. "Velocity Vector Estimation in Synthetic Aperture Flow and B-Mode Imaging," *IEEE*, 2004, 32-35.
Jensen, J. A., et al., "Equipment and methods for synthetic aperture anatomic and flow imaging," *IEEE Ultrasonics Symposium*, 2002, 1555-1564.
Jensen, J. A., "Range/velocity limitations for time-domain blood velocity estimation," *Ultrasound in Medicine and Biology*, 1993, 19(9), 741-749.
Jensen, J. A., "Directional Synthetic Aperture Flow Imaging," *IEEE Transactions on Ferroelectrics, and Frequency Control*, Sep. 2004, 51(9), 1107-1118.
Jensen, J. A., "Artifacts in blood velocity estimation using ultrasound and cross-correlation," *Medical and Biological Engineering and Computing*, 1994, 32/4(Suppl.), s165-s170.
Karaman, M. et al., "Synthetic Aperture Imaging for Small Scale Systems," *IEEE Transactions on Ferroelectrics, and Frequency Control*, May 1995, 42(3), 429-442.
Karaman, M. et al., "Adaptive Multi-element Synthetic Aperture Imaging with Motion and Phase Aberration Correction," IEEE Transactions on Ferroelectrics, and Frequency Control, Jul. 1998, 45(4), 1077-1087.
Karaman, M. et al., "VLSI Circuits for Adaptive Digital Beamforming in Ultrasound Imaging," *IEEE Transactions on Medical Imaging*, Dec. 1993, 12(4), 711-720.
Kasai, C. et al., "Real-Time Two-Dimensional Blood Flow Imaging Using an Autocorrelation Technique," *IEEE Transactions on Sonics and Ultrasonics*, May 1985, SU-32(3), 458-464.
Ketterling, J. A. et al., Operational Verification of a 40-MHz Annular Array Transducer, *IEEE Transactions on Ferroelectrics, and Frequency Control*, Mar. 2006, 53(3), 623-630.
Kim, J. H. et al., "Pipelined Sampled-Delay Focusing in Ultrasound Imaging Systems," *Ultrasonic Imaging*, 1987, 9, 75-91.
Linebarger, D. A. et al., "A Fast Method for Computing the Coarray of Sparse Linear Arrays," *IEEE Transactions on Antennas and Propagation*, Sep. 1992, 40(9), 1109-1112.

(56) References Cited

OTHER PUBLICATIONS

Lockwood, G. R. et al., "Real-Time 3-D Ultrasound Imaging Using Sparse Synthetic Aperture Beamforming," *IEEE Transactions on Ferroelectrics, and Frequency Control*, Jul. 1998, 45(4), 980-988.
Meng Xiangwei, "A Discussion of Second Order Sampling for Bandpass Signal," *Signal Processing Proceedings*, 1998, 51-52.
Nikolov, S. I. et al., "Three-Dimensional Real-Time Synthetic Aperture Imaging Using a Rotating Phased Array Transducer," *IEEE International Ultrasonics Symposium*, Munich, 2002, 2-5.
Nock, L. F. et al., "Synthetic Receive Aperture Imaging with Phase Correction for Motion and for Tissue Inhomogeneities—Part I: Basic Principles," *IEEE Transactions on Ferroelectrics, and Frequency Control*, Jul. 1992, 39(4), 489-495.
O'Donnell, M., "Coded Excitation System for Improving the Penetration of Real-Time Phased-Array Imaging Systems," IEEE Transactions on Ultrasonics, Ferrolectrics and Frequency Control, 1992, 39(3), 341-351.
O'Donnell, M. et al., Correlation-Based Aberration Correction in the Presence of Inoperable Elements, *IEEE Transactions on Ferroelectrics, and Frequency Control*, Nov. 1992, 39(6), 700-707.
Payne, P. A. et al., "Towards an Integrated Hand-Held Multi-Element Array Transducer for Ultrasound Imaging," *Acoustic Sensing and Imaging*, Mar. 29-30, 1993, Conference Publication No. 369, 13-16.
Powers, J. E., "Ultrasound Phased Array Delay Lines Based on Quadtrature Sampling Techniques," *IEEE Transactions on Sonics and Ultrasonics*, Nov. 1980, SU-27(6), 287-294.
USB Ultrasound Probe User Manual, Direct Medical Systems LLC, Aug. 2006.
Installation Manual, PUPS (Pocket Ultrasound Probe System, Direct Medical Systems LLC.
Tai K. Song and Song B. Park, A New Digital Phased Array System for Dynamic Focusing and Steering with Reduced Sampling Rate, *Ultrasonic Imaging*, 1990, 12, 1-16.
Tavli, B. et al., Correlation Processing for Correction of Phase Distortions in Subaperture Imaging, *IEEE Transactions on Ferroelectrics, and Frequency Control*, Nov. 1999, 46(6), 1477-1488.
Thomenius, K. E., "Evolution of Ultrasound Beamformers," *1996 IEEE Ultrasonics Symposium*, 1615-1622.
Tomov, B. G. et al., "Compact FPGA-Based Beamformer Using Oversampled 1-bit A/D Converters," *IEEE Transactions on Ferroelectrics, and Frequency Control*, May 2005, 52(5), 870-880.
Trahey, G. E. et al., "Synthetic Receive Aperture Imaging with Phase Correction for Motion and for Tissue Inhomogeneities—Part II: Effects of and Correction for Motion," *IEEE Transactions on Ferroelectrics, and Frequency Control*, Jul. 1992, 39(4), 496-501.
Vaughan, R. G. et al., "The Theory of Bandpass Sampling," *IEEE Transactions on Signal Processing*, Sep. 1991, 39(9), 1973-1984.
Ylitalo, J., "On the signal-to-noise ratio of a synthetic aperture ultrasound imaging method," European Journal of Ultrasound, 1996, 3, 277-281.
Zoltowski, M. D. et al., "Beamspace Root—MUSIC for Minimum Redundancy Linear Arrays," *IEEE Transactions on Signal Processing*, Jul. 1993, 41(7), 2502-2507.
From the International Searching Authority PCT Notification of Transmittal of the International Search Report and the Written Opinion of the International Searching Authority, or the Declaration, Dated Jul. 15, 2008, International Application No. PCT/US08/01399 12 pages.
From the International Searching Authority PCT Notification of Transmittal of the International Search Report and the Written Opinion of the International Searching Authority, or the Declaration, International Application No. PCT/US08/01397, Dated Jul. 15, 2008, 11 pages.
International Patent Application No. PCT/US2008/001399: International Preliminary Report on Patentability dated Mar. 4, 2009, 8 pages.
EP Search Report dated Oct. 24, 2014 from counterpart EP application No. 08 72 5088, 7 pages total.

\* cited by examiner

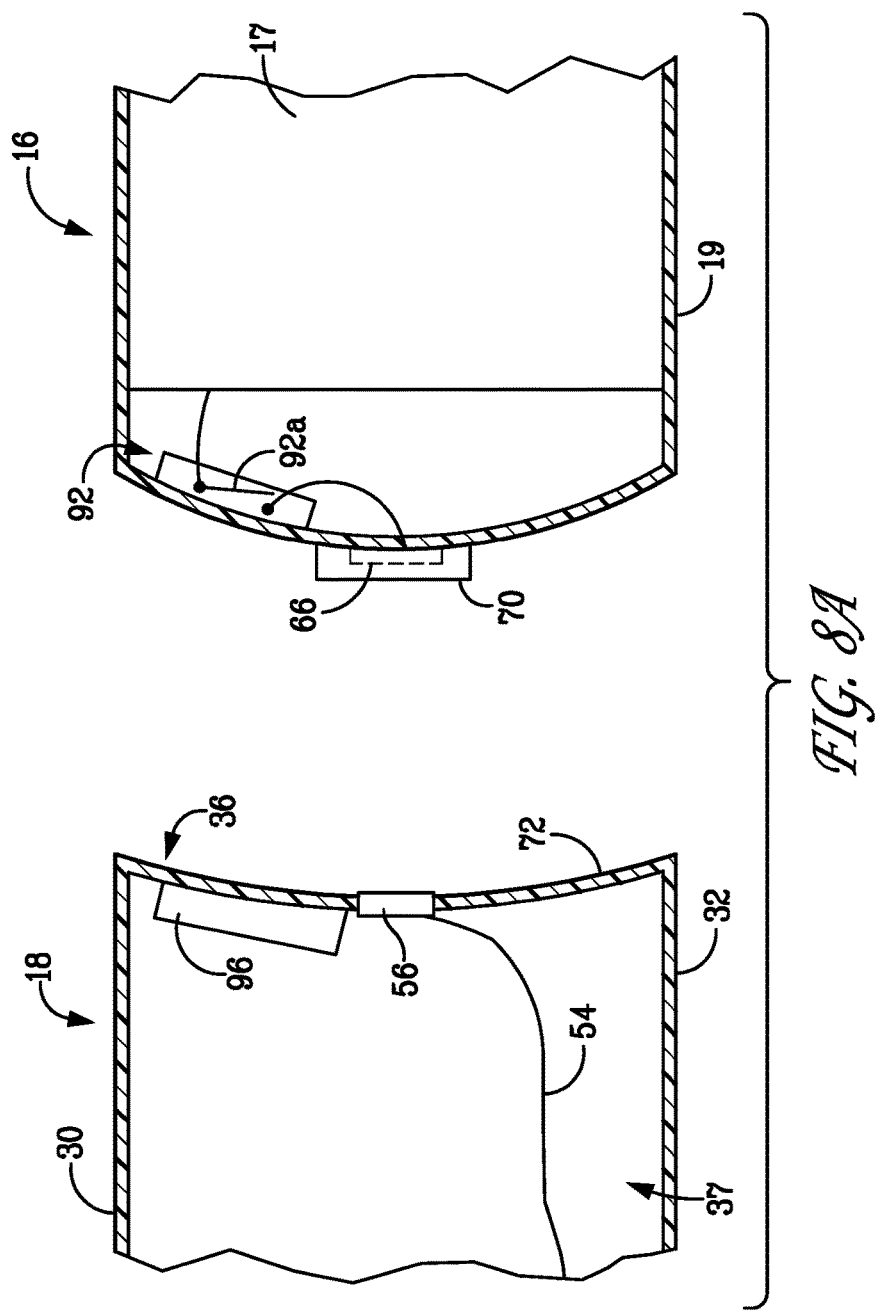

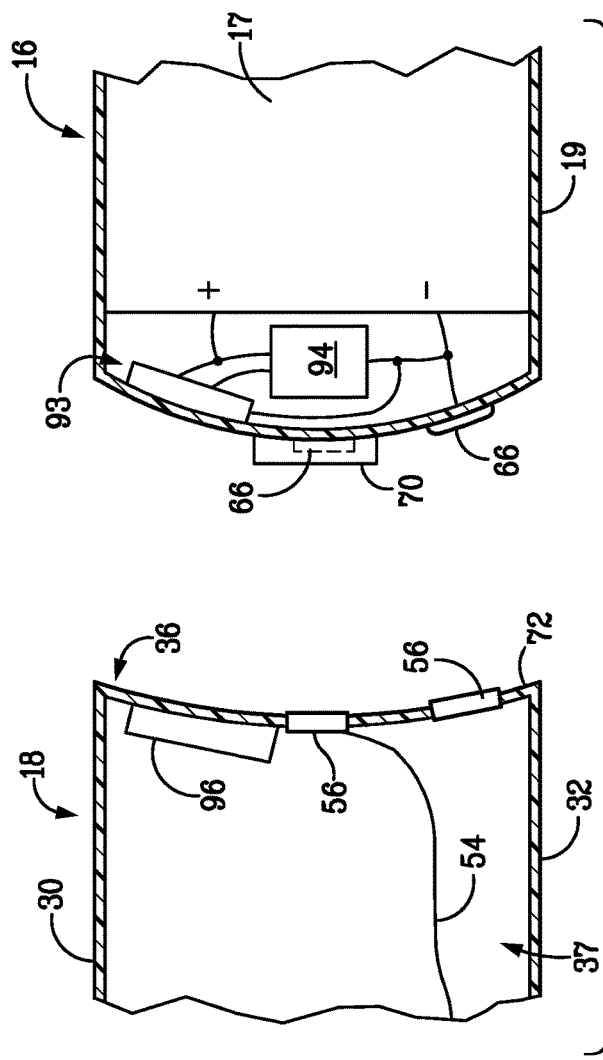
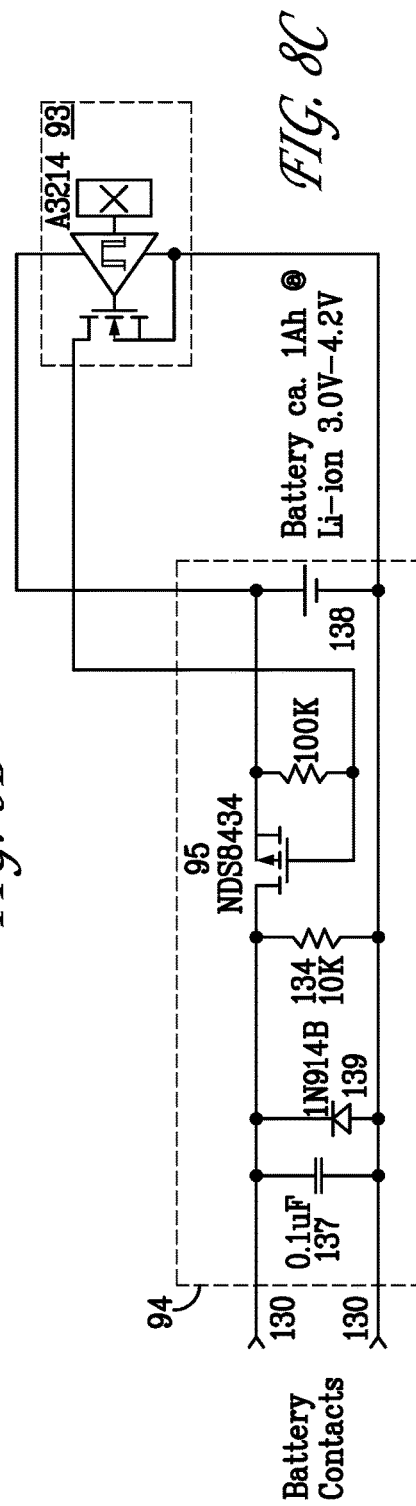
FIG. 8B
FIG. 8C

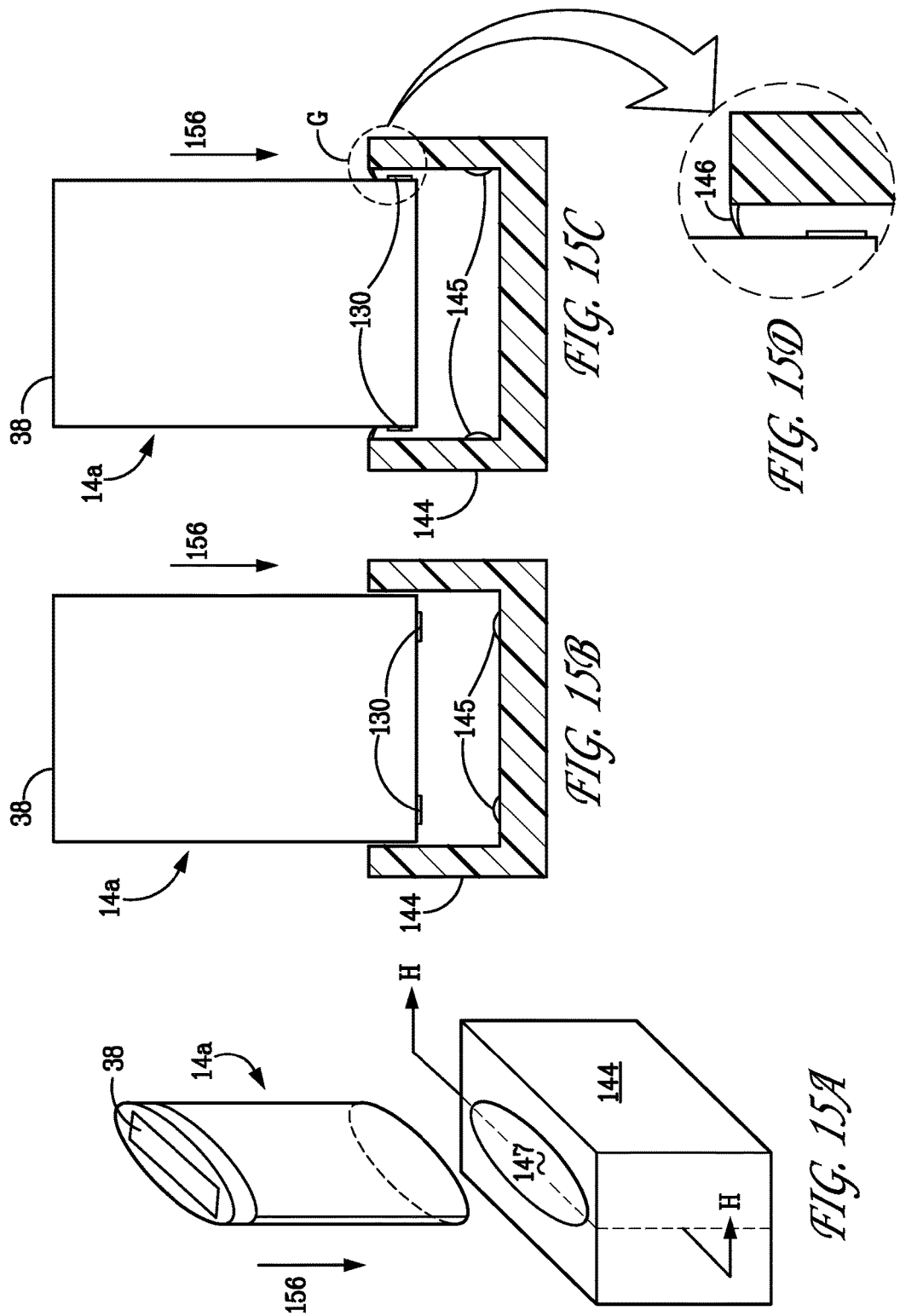

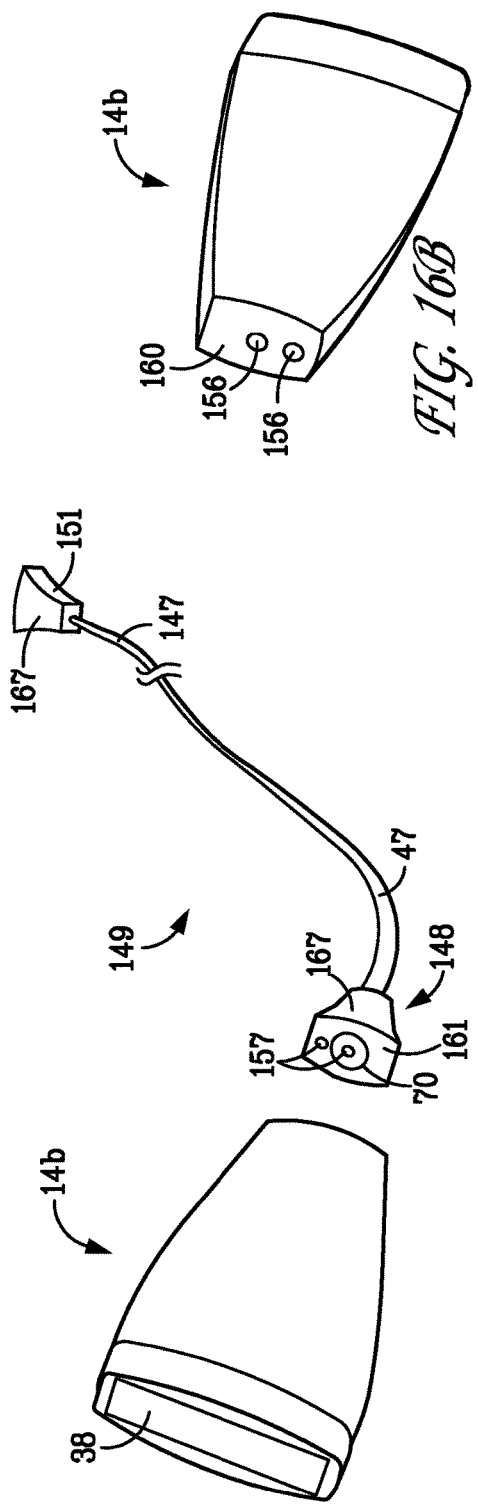
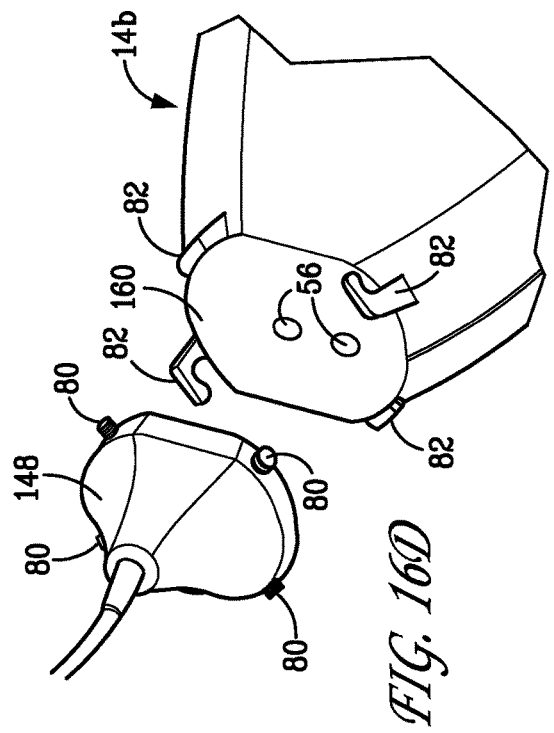
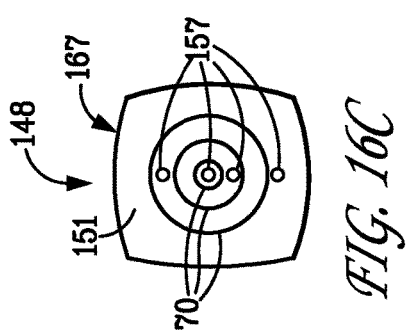
FIG. 16A
FIG. 16B
FIG. 16C
FIG. 16D

ULTRASOUND IMAGING SYSTEMS AND METHODS OF PERFORMING ULTRASOUND PROCEDURES

CROSS-REFERENCE TO RELATED APPLICATIONS

This application is related to: U.S. patent application Ser. No. 11/672,566, titled "Probes for Ultrasound Imaging Systems," filed Feb. 8, 2007; U.S. patent application Ser. No. 11/672,607, titled "Probes for Ultrasound Imaging Systems," filed Feb. 8, 2007; U.S. patent application Ser. No. 11/672,576, titled "Probes for Ultrasound Imaging Systems," filed Feb. 8, 2007; and U.S. patent application Ser. No. 11/672,596, titled "Methods for Verifying the Integrity of Ultrasound Probes," filed Feb. 8, 2007. The contents of each of these applications is incorporated by reference herein in its entirety.

TECHNICAL FIELD

The embodiments relate to ultrasound imaging systems. More particularly, the embodiments relate to probes that generate acoustical energy, and receive, process, and transmit information relating to return reflections of the acoustical energy.

BACKGROUND

Ultrasound imaging systems typically include a hand-held module commonly referred to as a probe or scan head. The probe can include one or more transducer arrays that emit acoustic vibrations at ultrasonic frequencies, e.g., approximately 1 MHz to approximately 20 MHz or higher.

The probe can be held against a patient's body so that the acoustical energy is incident upon a target area on or within the body. A portion of the acoustical energy is reflected back toward the probe, which senses the return reflections, or echoes. The transducer array generates an electrical output representative of the return reflections.

The probe is usually connected to the base unit via a multi-conductor cable. The base unit contains the circuitry necessary to stimulate the transducer to generate acoustic output waves and amplify and process the resulting echoes. The base unit processes the reflected signal information into a form suitable for display as a visual image, and displays the image on a monitor.

The use of a cable between the probe and the base unit can have disadvantages. For example, the relatively thick cable can interfere with the dexterity of the user in manipulating the probe. Moreover, the cable can degrade the electrical characteristics of the probe. In particular, the cable adds capacitance to the interfacing circuitry in the probe and the base unit. This additional capacitance can decrease the signal to noise ratio in the signals being transmitted through the cable. Also, the cable needs to be sterilized, or covered in a sheath that acts as a sterile barrier when the probe is used in a sterile environment, thus adding to the time and effort required to prepare the ultrasound imaging system for use.

The above-noted disadvantages of wired probes can be alleviated or eliminated through the use of a wireless probe, i.e., a probe that transmits information to the base unit by wireless means such as radio frequency (RF) signals. To facilitate wireless operation, a probe requires circuitry suitable to generate acoustic output waves and amplify and process the reflected acoustic echoes into a form suitable for sending over a wireless link.

A wireless probe needs to be equipped with a battery or other suitable power source. In applications where the probe is to be used in connection with a critical medical procedure, the service life of the battery, or the minimum interval between recharging, should be greater than the duration of the procedure. Ideally, the service life or recharging interval is substantially longer than the duration of a single procedure, so that the battery can be used throughout multiple procedures without being replaced or recharged.

The use of a battery can give rise to other needs unique to a battery-powered probe. For example, it may be necessary to monitor the charge state of the battery on a real-time basis, to ensure that that sufficient charge is left to perform a critical medical procedure.

Moreover, the probe and its battery may be equipped with electrical contacts to establish contact between the probe and a removable battery, or to facilitate charging of a non-removable battery. Because the probe may be exposed to electrically-conductive fluids, such as water or ultrasound coupling gel, the contacts on the probe need to be isolated from each other to prevent the unintended flow of electrical current therebetween. A need likewise exists to isolate the contacts on the battery from each other. Also, the probe should be sealed to prevent fluids from infiltrating into the interior of the probe and potentially damaging the electronic components housed within the probe.

Eliminating a cable between the probe and the base unit is believed to increase the potential for the probe to be accidentally dropped. A wireless probe therefore needs to be configured to withstand the mechanical shocks induced by impacts. One possible technique for providing impact resistance is potting the various electronic components within the probe. Potting, however, can prevent the servicing and re-use of the components. A need therefore exists to provide a wireless probe with impact resistance, while maintaining the capability to service or re-use the electronic components of the probe.

SUMMARY

Embodiments of probes for ultrasound imaging systems can be disassembled so that components located within housings of the probes can be re-used.

Embodiments of probes for ultrasound imaging systems comprise a transducer array that emits acoustical energy and receives return reflections of the acoustical energy, a circuit board, a transmitter mounted on the circuit board and communicatively coupled to the transducer array for transmitting information relating to the return reflections, and a housing comprising a backshell and a nosepiece removably attached to the backshell. The housing has an interior volume and the transducer array, the circuit board, and the transmitter are positioned in the interior volume.

Embodiments of probes for ultrasound imaging systems comprise a housing comprising an upper clamshell, a lower clamshell, and a nosepiece. The nosepiece and the upper and lower clamshells comprise interlocking features that secure the nosepiece to the first and second clamshells. The embodiments also comprise a transducer array that emits acoustical energy and receives return reflections of the acoustical energy, the transducer array being positioned within the housing.

Embodiments of probes for ultrasound imaging systems comprise a transducer array positioned within the housing. The transducer array emits acoustical energy and receives return reflections of the acoustical energy. The embodiments also include a transmitter communicatively coupled to the transducer array for transmitting information relating to the return reflections, and a housing having a nosepiece and a backshell. The transducer array is potted into the nosepiece, and the nosepiece is attached to the backshell by at least one of: interlocking joints formed on the nosepiece and the backshell; an adhesive having a bond strength that is lower than a yield strength of the material or materials from which the nosepiece is formed; fasteners; and latches.

Methods are provided for disassembling a probe for an ultrasound imaging system. The probe comprises a transducer array, a circuit board assembly communicatively coupled to the transducer array, and a housing comprising a nosepiece that forms a forward end of the housing and a clamshell pair attached to the nosepiece. The methods can comprise cutting the clamshell, removing a portion of the clamshell aft of the cut, and cutting or breaking a remaining portion of the clamshell.

Methods are provided for recovering components from an ultrasound imaging probe. The probe comprises a transducer array, a circuit board assembly communicatively coupled to the transducer array, a transmitter mounted on the circuit board and communicatively coupled to the transducer array, and a housing. The methods comprise determining that the probe is at least partially compromised; separating a portion of the housing in a way that renders the portion non-reusable; extracting a component from the probe; and re-using the extracted component.

Embodiments of probes for ultrasound imaging systems can include removable batteries. The embodiments can include electrically-insulative barriers surrounding contacts that facilitate electrical connections to the batteries. The embodiments can include switches that electrically isolate the batteries on a selective basis.

Embodiments of probes for ultrasound imaging systems comprise a housing, and a transducer array mounted in the housing. The transducer array directs acoustical energy at a target area and senses return reflections of the acoustical energy from the target area. The embodiments also comprise a transmitter mounted in the housing and communicatively coupled to the transducer array. The transmitter transmits information relating to the return reflections.

The embodiments also comprise a battery pack removably mounted to the housing. The battery pack provides electrical power for the transducer and the transmitter and comprises an enclosure, a rechargeable battery mounted within the enclosure, a first electrical contact mounted on the enclosure, and a switch electrically connected to the battery and the first electrical contact. The switch places the battery in electrical contact with the first electrical contact on a selective basis. The embodiments also comprise a second electrical contact mounted on the housing, wherein the second electrical contact mates with the first electrical contact when the battery pack is mounted to the housing.

Embodiments of probes for ultrasound imaging systems comprise a housing, and a transducer array mounted in the housing. The transducer array directs acoustical energy at a target area and senses return reflections of the acoustical energy from the target area. The embodiments also comprise a transmitter mounted in the housing and communicatively coupled to the transducer array. The transmitter transmits information relating to the return reflections.

The embodiments also comprise a battery pack removably mounted to the housing. The battery pack provides electrical power for the transducer and the transmitter and comprises an enclosure, a rechargeable battery mounted within the enclosure, a first electrical contact mounted on the enclosure. The embodiments also comprise a second electrical contact mounted on the housing. The second electrical contact mates with the first electrical contact when the battery pack is mounted to the housing.

The embodiments also comprise an electrically-insulative barrier mounted on the housing or the enclosure and surrounding the first electrical contact or the second electrical contact. The probe is drawn into a first position in relation to the housing as the probe and the charging station are partially mated. The housing and the charging station exert a compressive force on the gasket when the probe is in the first position. The probe backs away from the charging station as the probe moves from the first position to a fully mated position in relation to the charging station so that the compressive force decreases as the probe moves from the first position to the fully mated position.

Embodiments of probes for ultrasound imaging systems comprise a housing, and a transducer array mounted in the housing. The transducer array directs acoustical energy at a target area and senses return reflections of the acoustical energy from the target area. The embodiments also include a transmitter mounted in the housing and communicatively coupled to the transducer array. The transmitter transmits information relating to the return reflections.

The embodiments also include a battery pack mounted within the housing, and a first electrical contact mounted on the housing for mating with a second electrical contact on a charging station. The embodiments also include a switch electrically connected to the battery and the first electrical contact. The switch places the battery in electrical contact with the first electrical contact on a selective basis.

Embodiments of probes for ultrasound imaging systems can be configured to withstand being dropped or otherwise subjected to mechanical shock.

Embodiments of probes for ultrasound imaging systems comprise a housing, and a transducer array positioned within the housing. The transducer array emits acoustical energy and receives return reflections of the acoustical energy. The embodiments also comprise a circuit substrate positioned within the housing, and a compliant mount connecting the circuit substrate to the housing and substantially buffering the circuit substrate from mechanical shock.

Embodiments of probes for ultrasound imaging systems comprise a housing, and a transducer array positioned within the housing. The transducer array emits acoustical energy and receives return reflections of the acoustical energy. The embodiments also comprise at least one of a compliant bumper mounted on the housing and compliant cladding attached to an exterior surface of the housing.

Embodiments of probes for ultrasound imaging systems comprise a housing, and a transducer array positioned within the housing. The transducer array emits acoustical energy and receiving return reflections of the acoustical energy. The embodiments also include a circuit substrate communicatively coupled to the transducer array. At least a portion of the circuit substrate is potted and/or is covered by electronic circuit conformal coating. The embodiments further include a transmitter mounted on the circuit substrate and communicatively coupled to the transducer array for transmitting information relating to the return reflections.

Methods are provided for verifying that water and other fluids cannot reach the internal components probes for ultrasound imaging systems.

Methods for verifying watertight integrity of a probe for an ultrasound imaging system comprise introducing a gas into an interior volume of a housing of the probe, and determining whether the gas escapes from the interior volume.

Methods for verifying watertight integrity of a probe for an ultrasound imaging system comprise creating a vacuum within an interior volume of a housing of the probe; and determining whether gas from an ambient environment around the probe enters the interior volume.

Methods for verifying watertight integrity of a wireless probe for an ultrasound imaging system comprise immersing the probe in a liquid, applying a voltage between the probe and the liquid, and monitoring for a current above a predetermined level in response to the voltage.

Embodiments of wireless probes for ultrasound imaging systems comprise a housing, a transducer array positioned within the housing, the transducer array emitting acoustical energy and receiving return reflections of the acoustical energy; and a circuit substrate positioned within the housing. The embodiments also include a wireless transmitter mounted on the circuit substrate and communicatively coupled to the transducer array for transmitting information relating to the return reflections; and an electrically-conductive path between the circuit substrate and the housing.

Methods for verifying watertight integrity of a wireless probe for an ultrasound imaging system comprise applying a voltage and monitoring for a current above a predetermined level in response to the voltage.

Embodiments of ultrasound imaging systems comprise a probe, and a cable that can be removably connected to the probe.

Embodiments of ultrasound imaging systems comprise a probe comprising a housing, and a transducer array positioned within the housing. The transducer array emits acoustical energy and receives return reflections of the acoustical energy. The probe also comprises a transmitter mounted on the circuit substrate and communicatively coupled to the transducer array. The transmitter transmits stimulates the transducer array to emit acoustical energy. The embodiments also comprise a cable assembly comprising a first electrical connector capable of being removably connected to the probe.

Embodiments of ultrasound imaging systems comprise a probe comprising a housing, a first and a second electrical contact, and a transducer array positioned within the housing. The transducer array emits acoustical energy and receives return reflections of the acoustical energy. The embodiments also comprise a cable assembly comprising a first electrical connector capable of being removably connected to the probe. The first electrical connector comprises a third and a fourth electrical contact that mate with the respective first and second electrical contacts when the probe and the cable are mated. The embodiments also comprise an electrically-insulative barrier mounted on the probe or the connector so that the barrier encircles the first and third electrical contacts or the second and fourth electrical contacts when the probe and the cable are mated.

Methods for performing an ultrasound procedure comprise providing a probe comprising a housing and a transducer array positioned within the housing. The transducer array emits acoustical energy and receives return reflections of the acoustical energy. The methods also comprise providing a base unit that receives and processes output signals from the probe, providing a sterile cable assembly, removably connecting a first end of the cable assembly to the probe, and removably connecting a second end of the cable assembly to the base unit.

Embodiments of ultrasound imaging systems comprise a probe comprising a housing and a transducer array positioned within the housing. The transducer array emits acoustical energy and receives return reflections of the acoustical energy. The embodiments also comprise a cable assembly comprising a first electrical connector capable of being removably connected to the probe.

Methods for performing an ultrasound procedure comprise providing a probe comprising a housing and a transducer array positioned within the housing. The transducer array emits acoustical energy and receives return reflections of the acoustical energy. The methods also comprise providing a base unit that receives and processes output signals from the probe, and providing a sterile cable assembly. The methods also comprise removably connecting a first end of the cable assembly to the probe, and removably connecting a second end of the cable assembly to the base unit.

BRIEF DESCRIPTION OF THE DRAWINGS

The foregoing summary, as well as the following detailed description of embodiments, are better understood when read in conjunction with the appended diagrammatic drawings. For the purpose of illustrating the embodiments, the drawings diagrammatically depict specific embodiments. The appended claims are not limited, however, to the specific embodiments disclosed in the drawings. In the drawings:

FIG. 8A is a combined, magnified view of the areas designated "E" and "F" in FIG. 3;

FIG. 8B is a view taken from the perspective of FIG. 8A, depicting an alternative embodiment of the probe shown in FIGS. 1-8A;

FIG. 8C is a schematic illustration of a battery isolation circuit of the probe shown in FIG. 8B;

FIG. 15A is a perspective view of a probe having a non-removable battery, and a charging stand for use with the probe;

FIGS. 15B and 15C are side views of the probe and charging stand shown in FIG. 15A, depicting a cross section of the charging stand taken along the line "H-H" of FIG. 15A, depicting charging contacts of the probe in different locations on the probe, and depicting the probe partially inserted in the charging stand;

FIG. 15D is a magnified view of the area designated "G" in FIG. 15C;

FIG. 16A is a perspective view of a probe, and a cable assembly that can be removably connected to the probe;

FIG. 16B is a perspective view of the probe shown in FIG. 16A;

FIG. 16C is a front view of an electrical connector of the cable assembly shown in FIG. 16A;

FIG. 16D is a perspective view of the probe and a cable assembly shown in FIGS. 16A-16C, equipped with arms and projections that secure the probe and cable assembly together;

DETAILED DESCRIPTION OF ILLUSTRATIVE EMBODIMENTS

Figure 1:
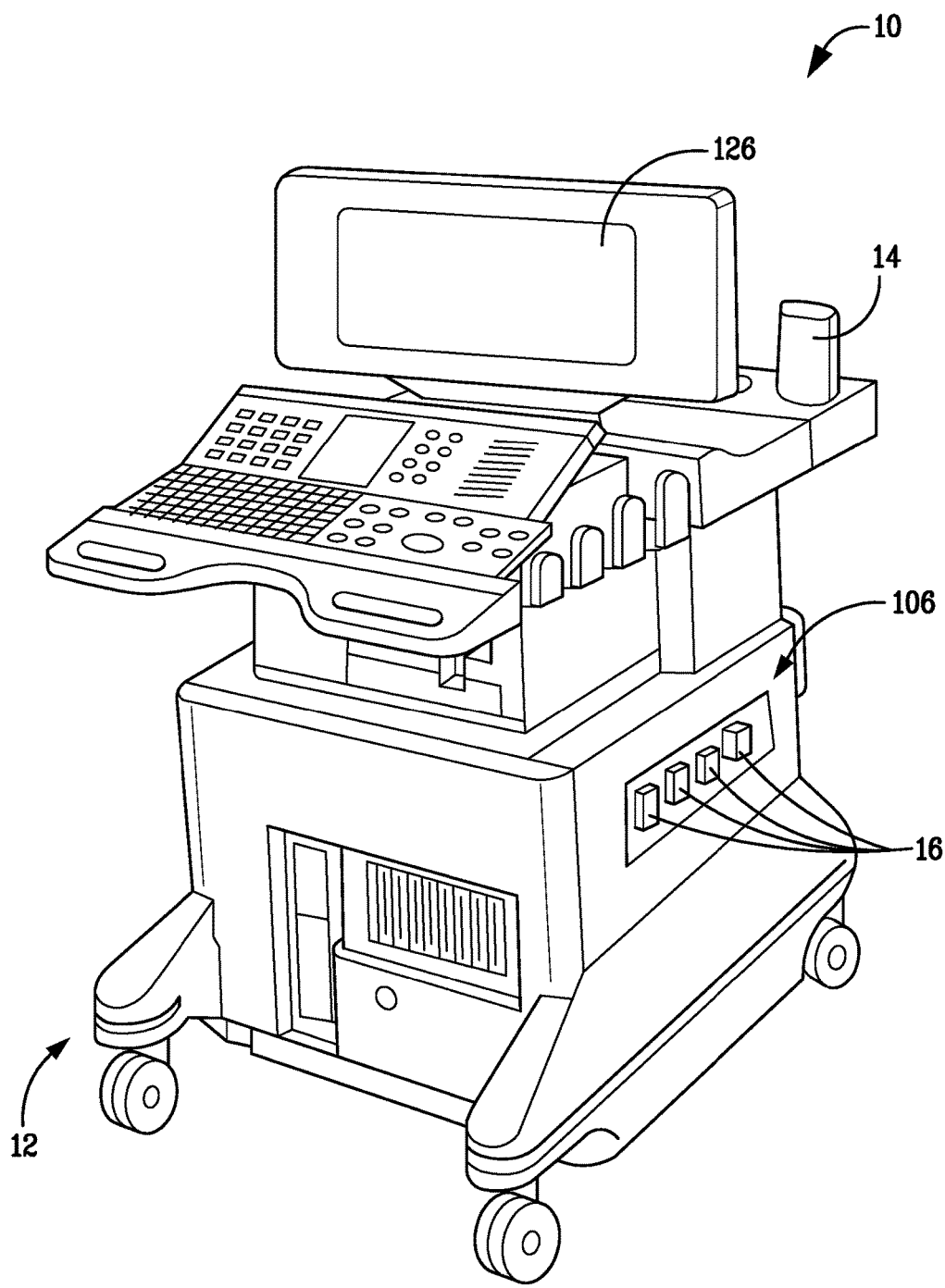
FIG. 1 is a perspective view of an embodiment of an ultrasound imaging system.

FIGS. 1-8 and 10-12 depict an embodiment of an ultrasound imaging system 10. The system 10 includes a base unit 12 and a probe 14, as shown in FIG. 1. The probe 14 can be a wireless probe, i.e., the probe 14 can communicate with the base unit 12 by wireless means such as, but not limited to ultra-wideband, spread-spectrum RF signaling.

Figure 2:
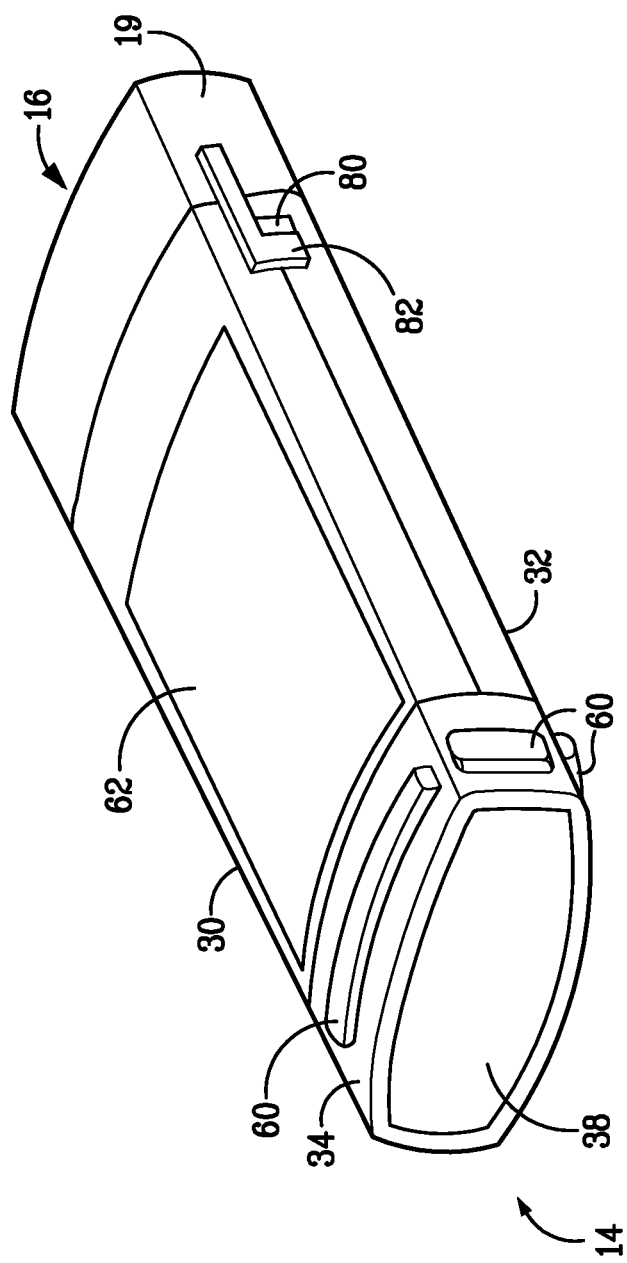
FIG. 2 is a top perspective view of an embodiment of a probe of the ultrasound imaging system shown in FIG. 1.
Figure 3:
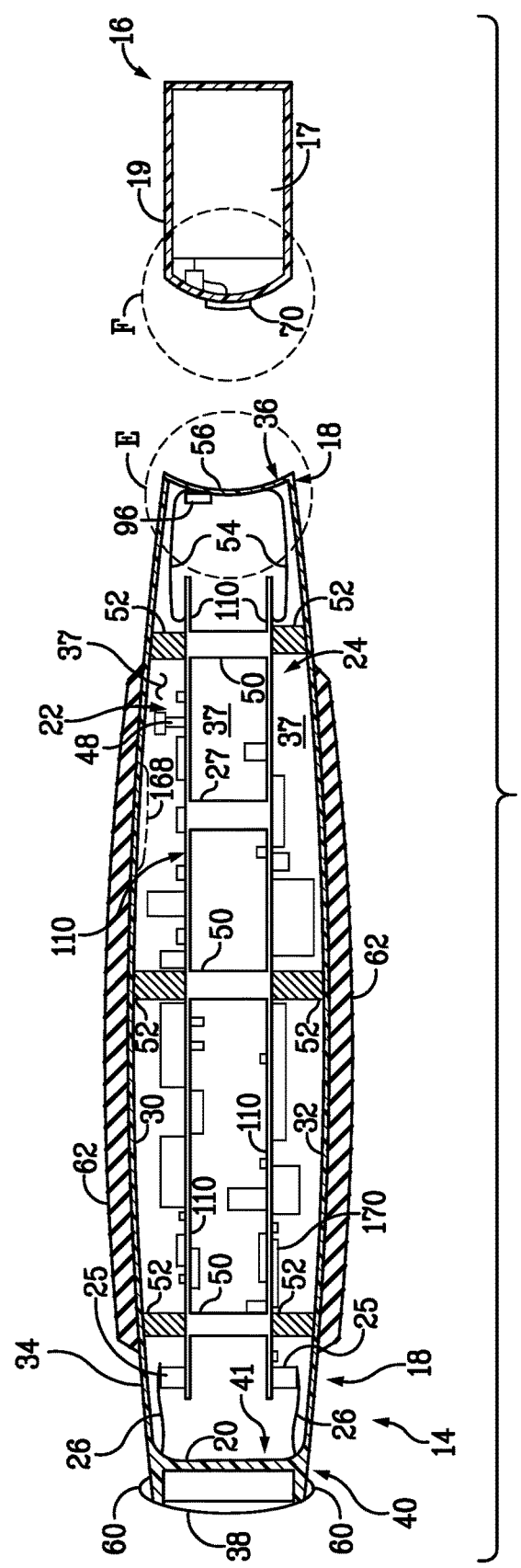
FIG. 3 is a side view of the probe depicted in FIGS. 1 and 2, with a side of a housing of the probe made transparent so that internal components of the probe are visible, and with a battery and the housing of the probe in an un-mated state.
Figure 4:
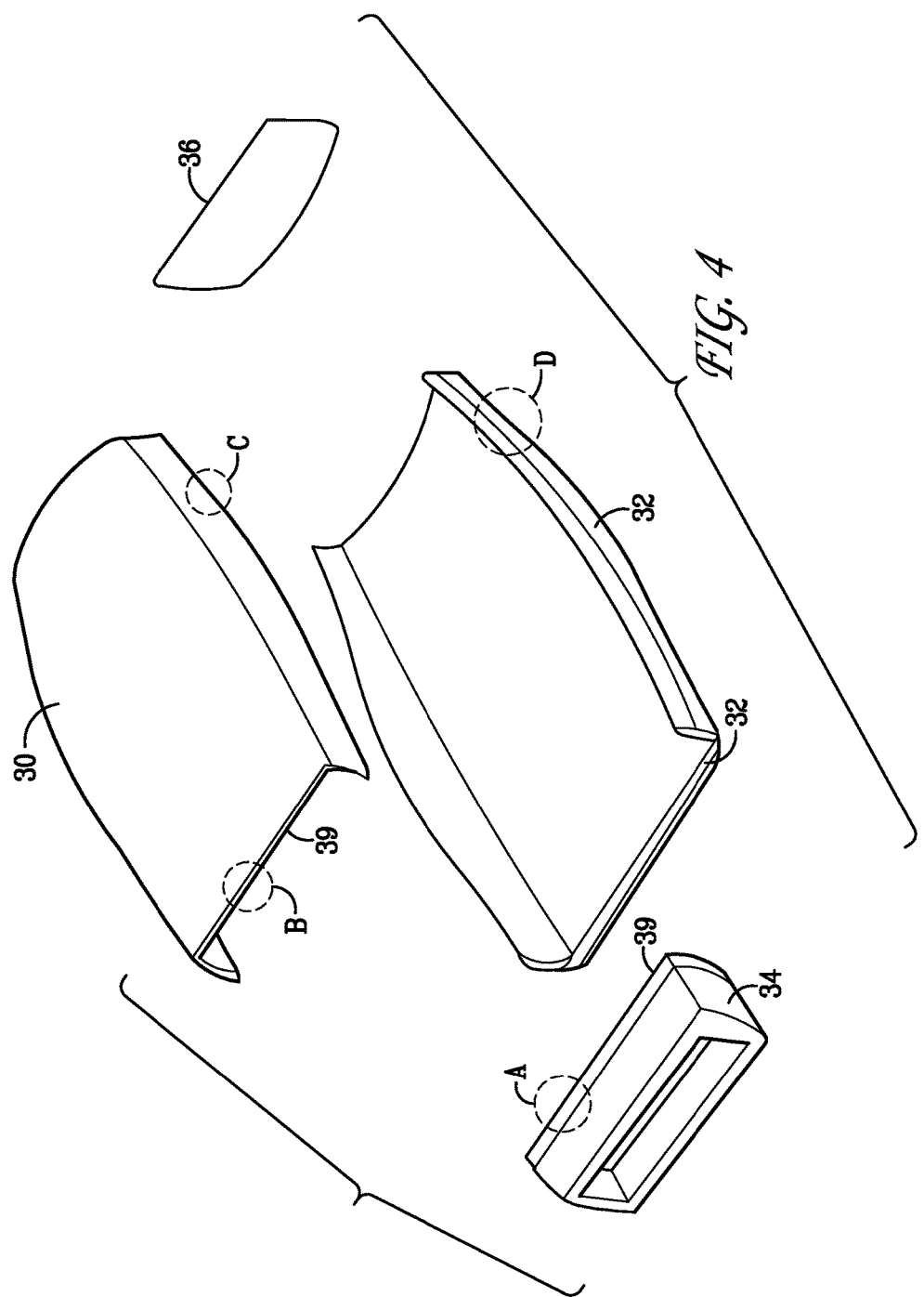
FIG. 4 is an exploded view of the housing of the probe shown in FIGS. 1-3, without the internal components of the probe.

The probe 14 comprises a housing 18 and a transducer array 20 mounted in the housing 18, as shown in FIGS. 2-4. The probe 14 can also include an externally-mounted battery pack 16. The battery pack 16 comprises a rechargeable battery 17 and a sealed enclosure 19 that houses the battery 17. The battery pack 16, as discussed below, can be mated with and removed from the housing 18 by the user, so that the battery pack 16 can be charged by itself, i.e., without the remainder of the probe 14. The battery 17 can be a Lithium-ion type, such as an assembly of three type LPP402934 cells available from Varta Microbattery Gmbh, Ellwangen, Germany.

The base unit 12 can incorporate a charging station 106, shown in FIG. 1, that recharges and maintains the charge state of multiple battery packs 16. By having a multi-bay charging station 106 on the base unit 12, a ready supply of fully charged battery packs is available to replace a battery pack 16 that has become depleted in use.

The housing 18 can include an upper clamshell 30, a lower clamshell 32, a nosepiece 34, a battery panel 36, and an acoustic window 38, as shown in FIGS. 3 and 4. The upper clamshell 30, lower clamshell 32, and battery panel 36 form a backshell 42 of the housing 18. The battery panel 36 can be unitarily formed with one or both of the upper and lower clamshells 30, 32, in the alternative. The entire backshell 42, i.e., the upper and lower clamshells 30, 32 and the battery panel 36, can be unitarily formed in other alternative embodiments.

The transducer array 20 and the acoustic window 38 are mounted on the nosepiece 34. The upper and lower clamshells 30, 32, the nosepiece 34, and the battery panel 36 can be formed from a relatively low cost, shatter-resistant polymer such as an ABS-Polycarbonate blend available, for example, from General Electric Plastic as the Cycoloy series resins, using a suitable process such as conventional die-casting.

The overall length of the housing 18 can be approximately 6 cm to approximately 10 cm. A specific range of values for the length of the housing 18 is presented for exemplary purposes only; the length of the housing 18 can be less than 6 cm and greater that 10 cm.

The transducer array 20 emits acoustical energy. The transducer array 20 can produce acoustical vibrations having frequencies in the ultrasonic range, e.g., approximately 1 MHz to approximately 20 MHz or higher. The acoustical vibrations, when incident upon a target area on a patient, generate return reflections or echoes. The transducer array 20 senses the acoustic reflections, and generates an electrical output representative of the acoustic reflections.

The transducer array 20 can include, for example, a first plurality of piezoelectric elements that, when energized, generate the acoustical vibrations in the ultrasonic frequency range. The transducer array 20 can also include, for example, a second array of piezoelectric elements that generate an electrical output in response the return reflections incident thereon. Transducer arrays configured in other manners can be used in the alternative. Transducer arrays suitable for use as the transducer array 20 can be obtained, for example, from Sound Technology, Inc. of State College, Pa. as the model 6L128 transducer array.

The probe 14 also includes a first circuit board assembly 22 and a second circuit board assembly 24 mounted in the housing 18, as shown in FIG. 3. The first and second circuit board assemblies 22, 24 can be communicatively coupled to each other by, for example, conventional board-to-board electrical connectors 27.

Each of the first and second circuit board assemblies 22, 24 is communicatively coupled to the transducer array 20 by an associated electrical connector 25 and an associated cable, as shown in FIG. 3. The cable can be a flexible printed wire board (PWB) 26 or other type of non-rigid connecting means that can withstand repeated flexing. Each electrical connector 25 can be mechanically connected to the associated first or second circuit board assembly 22, 24 in a manner that prevents the interface between the electrical connector 25 and the first or second circuit board assembly 22, 24 from flexing. For example, the housing of each electrical connector 25 can be secured to the associated first or second circuit board assembly 22, 24 by a rigid standoff.

The first and second circuit board assemblies 22, 24 include the various electronic components that stimulate the probe 14 with electrical energy, amplify, digitize, and otherwise process the output of the transducer array 20, package the processed signals for transmission to the base unit 12, and transmit the data for subsequent processing, recording, and/or display by the base unit 12.

For example, the first or the second board assembly 22 can include a transmit controller 109, a transmitter that is referred to as a transmit pulser 107, a transmit receive switch 105, a receive amplifier 108 that amplifies the output of the transducer array 20, a time-varying gain control (TGC) circuit 114, an analog-to-digital converter 118, a receive data processor 116, and a transceiver 122. These components are illustrated diagrammatically in FIG. 7.

The first and second circuit board assemblies 22, 24 each include a circuit substrate such as a circuit board 110 depicted in FIG. 3. The receive amplifier 108, transmit controller 109, transmit pulser 107, transmit receive switch 105, TGC circuit 114, analog-to-digital converter 118, receive data processor 116, and transceiver 122 can be mounted on the circuit board 110 of the first or the second circuit board assembly 22, 24.

The transmit pulser 107 is a driver circuit that preferably takes TTL logic level signals from the transmit controller 109, and provides relatively high-power drive to the transducer array 20 to stimulate it to emit acoustic waves. The transmit controller 109 can act as a transmit beamformer that provides appropriately timed transmit signals to the transmit pulser 107 to form steered and focused transmit beams of acoustic energy in a conventional manner well understood in the art. The transmit controller 109 can be made considerably simpler if it is only necessary to generate unfocused or divergent acoustic pulses for a small number of elements, as for use with synthetic focusing techniques, which are also well understood in the art.

The transmit/receive switch 105 protects the low-voltage TGC circuit 114 from the relatively high-voltage pulses generated by the transmit pulser 107. When receiving echoes from the patient's body, the transmit/receive switch 105 connects the low voltage echo signals from the transducer array 20 to the input of the TGC circuit 114. The TGC circuit 114 amplifies the output signals of the transducer array 20 to levels suitable for subsequent processing. The TGI circuit 114 compensates for the attenuation of the acoustical energy emitted by the probe 14 as the energy travels though human tissue before reaching the target area on the patient. The TGC circuit 114 also drives the analog-to-digital converter 118.

The receive data processor 116, if acting as a receive data beamformer, delays and sums the digitized echo output signals of the transducer array 20, to dynamically focus the signals so that an accurate image of the target area can be produced by the base unit 12, in a way that is well understood in the art. Alternatively, the receive data processor 116 can arrange, compress, and package the echo signal digital data, without performing receive beamforming. The receive data sets for all transmit elements can be sent to the transceiver 122 when using synthetic focusing techniques for beamforming.

The transceiver 122 transmits the digitized output of the receive data processor 116 to the base unit 12. The transceiver 122 can also receive inputs from the base unit 12. The transceiver 122 can communicate with a compatible transceiver 123 on the base unit 12 by way of ultra-wideband RF signaling.

Transmitters that communicate by wireless means other than RF signals, such as but not limited to infrared or optical signals, can be used in the alternative to the RF transceivers 122, 123. Moreover, alternative embodiments can include a transmitter in lieu of the transceiver 122, to facilitate one-way communication from the probe 14 to the base unit 12. The term "transmitter," as used in the appended claims, is intended to encompass transceivers that facilitate two-way communications, one-way transmitters, and other transmitting devices.

In another embodiment, communications between base unit 12 and probe 14 can be facilitated over a wired link, using a small number of signal conductors. In this case, the transceivers 122 and 123 can be less complex due to the reduced functionality required thereof. The wired link could also carry power from the base unit 12 to the probe 14, obviating the need for the battery 17. The wired link can comprise electrical, optical, or other types of signal conductors.

In another embodiment, the analog signals from the TGC circuit 114 can be processed in a charge-coupled device receive beamformer or other analog beamformer, instead of in the analog-to-digital converter 118 and the receive data processor 116. In this case, the output from the analog receive beamformer can be digitized, and the digital data can be communicated to the base unit 12 through the transceiver 122 in the normal manner. Alternatively, the analog beamformer output can be sent to the base unit 12 by the transceiver 122 as an analog signal, and then digitized in the base unit 12 and displayed on the monitor 126. The analog signal can be sent to the base unit 12 over a wireless or wired link, in a manner similar to that discussed above in relation to the digital data. The analog signal can be the modulation source of an AM of FM modulated RF carrier channel between the transceivers 122 and 123.

Figure 7:
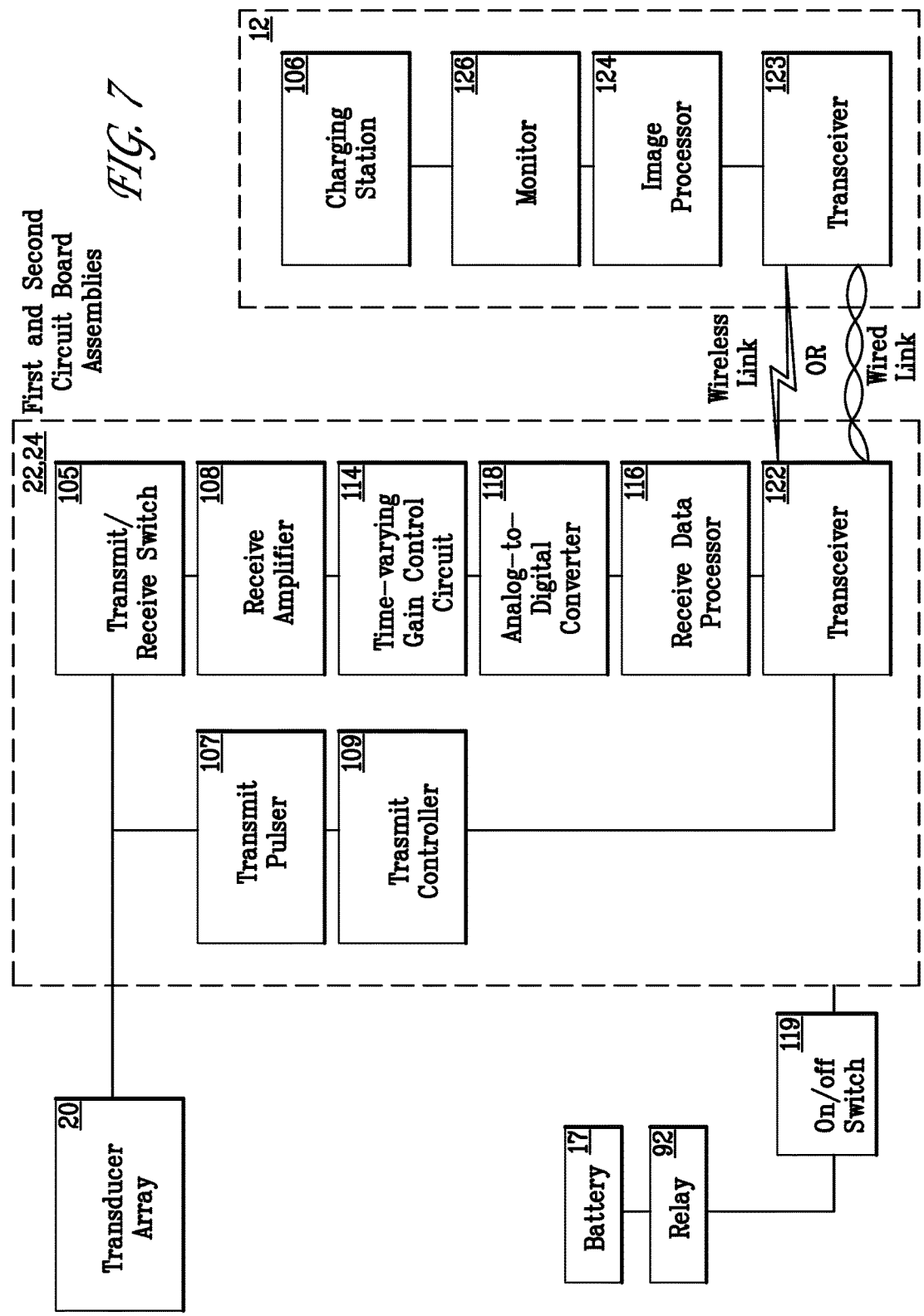
FIG. 7 is a block diagram depicting electrical and electronic components of the probe and base unit shown in FIGS. 1-6.

The base unit 12 includes an image processor 124 and a monitor 126, as shown in FIGS. 1 and 7. The image processor 124 forms an image of the target area on the patient based on the signal received from the probe 14, and displays the image on the monitor 126.

Specific details of the various electronic components of the probe 14 are presented for exemplary purposes only. Alternative embodiments can have electronic components configured in other manners.

Each of the first and second circuit board assemblies 22, 24 is communicatively coupled to the battery pack 16 by way of an associated lead 54, and an associated contact 56 mounted on the battery panel 36, as shown in FIG. 3. Each lead 54 can be formed from a non-rigid material that can withstand repeated flexing. Each lead 54 can be mechanically connected to the circuit board 110 of the associated first or second circuit board assembly 22, 24, in a manner that prevents the interface between the lead 54 and the circuit board 110 from flexing. For example, the end portion of each lead 54 can be fixed to the associated circuit board 110 by a suitable means such as epoxy, to immobilize the lead 54 at some distance prior to the electrical interface between the lead 54 and the first or second circuit board assembly 22, 24.

The probe 14 can include a user-activated on/off switch 119, shown in FIG. 7, to electrically isolate the first and second circuit board assemblies 22, 24 from the battery 17 on a selective basis.

The upper clamshell 30, lower clamshell 32, nosepiece 34, and battery panel 36 define an interior volume 37 within the probe 14, as shown in FIG. 3. The transducer array 20 and the first and second circuit board assemblies 22, 24 are positioned within the interior volume 37.

The nosepiece 34, transducer array 20, and acoustic window 38 together form a nosepiece subassembly 40 that can be checked for functionality before the probe 14 is assembled. The transducer array 20 and the proximal portions of the PWBs 26 can be potted into the nosepiece 34 using an epoxy backfill 41, as shown in FIG. 3.

The acoustic window 38 covers the forward end of the nosepiece 34, and is formed from an acoustically-transparent material. The acoustic window 38 is securely attached to the nosepiece 34 using, for example, an adhesive. The acoustic window 38 is positioned in front of the transducer array 20, so that the acoustical vibrations generated by the transducer array 20 and the resulting return reflections pass through the acoustic window 38.

Figure 6:
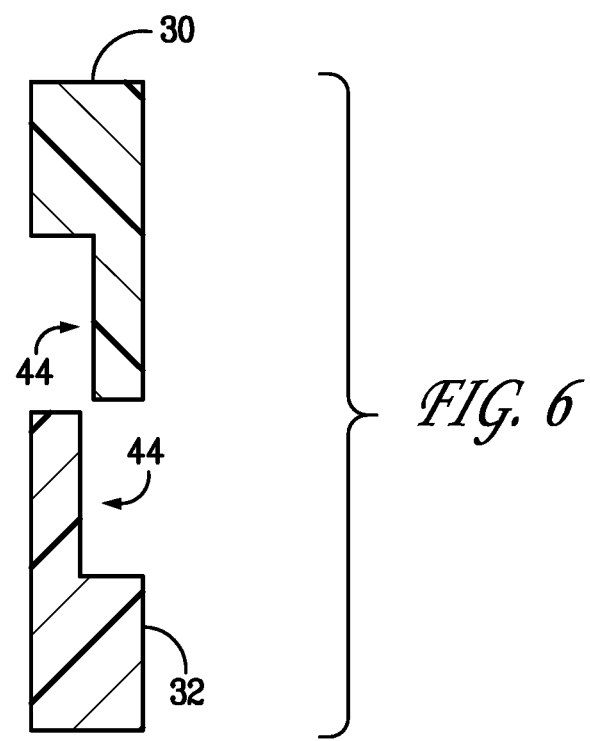
FIG. 6 is a combined, magnified view of the areas designated "C" and "D" in FIG. 4, depicting the upper and lower clamshells of the housing in cross-section, as the upper and lower clamshells are mated with each other.

The upper and lower clamshells 30, 32 are attached to each other along longitudinally-extending joints 44, as shown in FIG. 6. The nosepiece 34 is attached to the forward edges of the upper and lower clamshells 30, 32. The battery panel 36 is attached to rearward edges of the upper and lower clamshells 30, 32. The upper and lower clamshells 30, 32, nosepiece 34, and battery panel 36 can be removably attached to each other, as discussed below. The term "removably attached," as used herein, means attached in a manner that permits the attached components to be detached from each other without substantially damaging the components or otherwise detrimentally affecting the potential for the components to be re-used.

The probe 14 can be made waterproof. More particularly, each interface between the various component parts of the housing 18 can be sealed so that water, ultrasound coupling gel, and other fluids cannot enter the interior volume 37 within the housing 18. Also, the housing 18 can be configured so that the transducer array 20 and the first and second circuit board assemblies 22, 24 can be accessed without being damaged. This feature, as discussed below, permits the relatively expensive transducer array 20 to be removed from the housing 18 for service and/or use in another probe 14.

The upper clamshell 30 can be secured to the lower clamshell 32 using an adhesive having a relatively high bond strength applied to the joints 44. For example, MA3940 adhesive, available from ITW Plexus, Danvers, Mass., can be used in this application. A typical shear strength for this type adhesive is about 10 MPa. The battery panel 36 can be secured to the upper and lower clamshells 30, 32 using the same high-strength adhesive. The use of an adhesive having a relatively high bond strength can obviate the need to equip the upper and lower clamshells 30, 32 and the battery panel 36 with interlocking features to secure these components to each other. For example, the use of a relatively strong adhesive between the upper and lower clamshells 30, 32 permits the use of the relatively simple and compact joint 44 depicted in FIG. 6.

The nosepiece 34 can be secured to the upper and lower clamshells 30, 32 using an adhesive having a relatively low bond strength, i.e., a bond strength that is lower than the yield strength of the material from which the nosepiece 34 is formed, to facilitate removal of the nosepiece subassembly 40 and the first and second circuit board assemblies 22, 24 from the probe 14. For example, RTV110 adhesive, available from GE Advanced Materials of Wilton, Conn., can be used in this application. A typical shear strength for this type of adhesive/sealant is about 0.67 MPa.

The low-strength adhesive should be compatible with the high-strength adhesive; contact between the low and high strength adhesives need to be avoided in applications where the two types of adhesives are not compatible. For example, RTV silicone adhesives can greatly reduce the adhesion of other adhesives, once the RTV has contacted the surface to be bonded. To accommodate such incompatible adhesives, the upper and lower clamshells 30, 32 should be first bonded together, the bonding adhesive should be allowed to fully cure, and the assembled backshell 42 should then be bonded to the nosepiece 34.

As the upper and lower clamshells 30, 32 are formed from a relatively inexpensive material, these components can be sacrificed to gain access to the relatively expensive components within the probe 14 to facilitate servicing and repair of the probe 14. In particular, the upper and lower clamshells 30, 32 can be carefully cut just aft of the nosepiece 34. The electrical connectors 25 can then be disconnected from the circuit boards 22, 24 so that the majority of the upper and lower clamshells 30, 32 and the circuit boards 22, 24 can be removed from the nosepiece 34. In addition, the backshell 42 can be carefully cut apart along the seam lines between the upper and lower clamshells 30, 32, and the electrical connector 27 can be disengaged to expose the circuit boards 22, 24. The circuit boards 22, 24 can then be serviced and reused.

The remaining portions of the upper and lower clamshells 30, 32, still attached to the nosepiece 34, can be cut or broken at one point along their respective circumferences. The remaining portions can then be pried, peeled, or otherwise detached from the joint of the nosepiece 34. The relatively low-strength adhesive used to attach the nosepiece 34 to the upper and lower clamshells 30, 32 can facilitate removal of the remaining portions of the upper and lower clamshells 30, 32 with minimal difficulty. The nosepiece subassembly 40 and the first and second circuit board assemblies 22, 24 can subsequently be serviced or repaired, and reused.

The overlap of the contacting surfaces of the joints between the nosepiece 34 and the upper and lower clamshells 30, 32 can be larger than the overlap of the contacting surfaces of the joints 44 between the upper and lower clamshells 30, 32. This feature can provide additional surface area for the relatively weak adhesive used in the joints between the nosepiece 34 and the upper and lower clamshells 30, 32.

Alternatively, the nosepiece 34 and the upper and lower clamshells 30, 32 can be equipped with interlocking features, to augment the relatively low-strength adhesive used to secure these components to each other.

Figure 5:
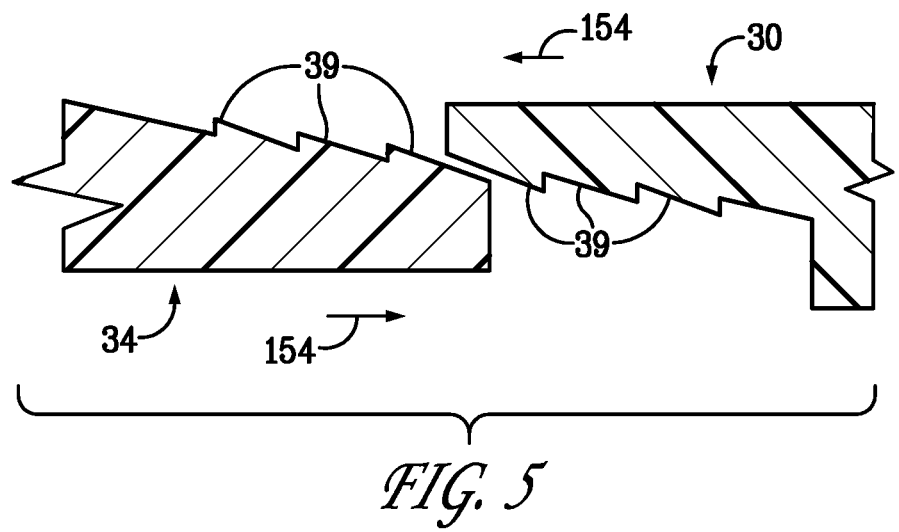
FIG. 5 is a combined, magnified view of the areas designated "A" and "B" in FIG. 4, depicting upper and lower clamshells of the housing in cross-section, as the upper and lower clamshells are mated with a nosepiece of the housing.

For example, the joints between the nosepiece 34 and the upper and lower clamshells 30, 32 can have a saw-tooth configuration as depicted in FIG. 5. The forward ends of the upper and lower clamshells 30, 32 can have a complementary saw-tooth configuration. The saw-tooth joints include teeth 39 that cause the rearward end of the nosepiece 34 and the forward ends of the upper and lower clamshells 30, 32 to resiliently deflect outwardly, away from each other, as the nosepiece 34 and the upper and lower clamshells 30, 32 are moved toward each other during assembly, in the relative directions denoted by the arrows 154 in FIG. 5. The upper and lower clamshells 30, 32 should be attached to each other before the upper and lower clamshells 30, 32 are attached to the nosepiece 34.

The rearward end of the nosepiece 34 and the forward ends of the upper and lower clamshells 30, 32 snap inwardly, toward each other, as the nosepiece 34 and the upper and lower clamshells 30, 32 are fully mated. The engagement of the teeth 39 on the nosepiece 34 and the upper and lower clamshells 30, 32 helps to secure the nosepiece 34 to the upper and lower clamshells 30, 32. Other types of interlocking features such as latches or fasteners can be used in lieu of saw-tooth joints in alternative embodiments.

The interface between the upper and lower clamshells 30, 32 of alternative embodiments can be equipped with interlocking features, such as the saw-tooth joints described above. Interlocking features can also used at the interface between the battery panel 36 and the upper and lower clamshells 30, 32 of alternative embodiments. The use of interlocking features at these locations can eliminate the need to use two different types of adhesives to assemble the housing 18. Interlocking features may consume additional space within the housing 18, however, and therefore may be unsuitable in applications where space within the housing 18 is limited.

In embodiments where the various components of the housing 18 are held together by interlocking features, latches, fasteners, etc., techniques other than adhesives can be used to seal the joints between the components. For example, the joints can be sealed using a grease such as Nyogel 774VHF, available from Nye Lubricants of Fairhaven, Mass. This grease is highly viscous over an operating range of about 10° C. to about 50° C., and is substantially waterproof. The grease therefore would prevent ultrasound gel or other liquids from penetrating the joints. A high-melting-point wax such as Caranuba wax can also be used as a sealing material. A gasket formed from a highly compliant material such as EPDM rubber can be used to provide a seal between the various components of the housing 18 in other alternative embodiments. The sealing techniques noted in this paragraph permit the various components of the housing 18 to be disassembled without damage thereto.

The probe 14 can include features that permit the probe 14 to withstand mechanical shocks resulting from impacts and other abuse. In particular, the first and second circuit board assemblies 22, 24 can be constructed in a manner that minimizes the sensitivity of the first and second circuit board assemblies 22, 24 to impact loads.

For example, the first and second circuit board assemblies 22 can include components that are inherently tolerant of mechanical shock. Components such as capacitors can be chosen so as to have a relatively low aspect ratio. For good mechanical strength, the ratio of the component height to its smallest mounting base dimension should be about 0.2 or less. If the component height is too high compared to the size of its mounting base, the leads attaching the component to the circuit board 22, 24 may be subjected to large forces if the probe is dropped. The leads may break upon impact, or gradually fatigue if subjected to repeated smaller impacts. Moreover, the various electronic components of the first and second circuit board assemblies 22, 24 can be chosen to have relatively robust electrical leads, to further reduce the likelihood of breakage of the leads.

Components of the first and second circuit board assemblies 22, 24 that are not inherently shock-resistant can be protected from impact loads by immobilizing those particular components. For example, a relatively fragile component can be affixed to an adjacent component having greater shock resistance and strength. Alternatively, a relatively fragile component can be affixed directly to the underlying circuit board 110 in a mechanically robust manner by, for example, affixing the component to a bracket 48 that bears the weight of the component, stabilizes the component in the event of an impact, and transfers the impact forces from the body of the component to the associated circuit board 22, 24. The bracket can be securely attached to the circuit board 22, 24 by, for example, machine or sheet metal screws of sufficient size to bear the impact load.

Alternatively, relatively fragile components can also be potted on an individual basis, if disassembly and re-use of the component is not required or desired. Alternatively, all or a portion of the first and second circuit board assemblies 22, 24 can be potted, or the first and second circuit board assemblies 22, 24 can be potted to form a single block.

Another alternative for increasing the ruggedness of the various electronic components of the first and second circuit board assemblies 22, 24 comprises coating the circuit boards 110 with a material such as PC12-0007M, available from Henkel, Inc. of Irvine, Calif., that surrounds and encapsulates the components on the circuit boards 110 in a manner that renders the components more tolerant of shock and vibration. Other electronic circuit conformal coatings can be used in the alternative.

The entire interior volume 37 of the housing 18 can be potted in other alternative embodiments, to increase the ruggedness of the first and second circuit board assemblies 22, 24. This approach can eliminate the need, discussed below, for compliant standoffs between the first and second circuit board assemblies 22, 24 and the housing 18. Potting the entire interior volume 37 can also protect the first and second circuit board assemblies 22, 24 from leakage of water, ultrasound coupling gel, and other fluids into the interior volume 37. Potting the entire interior volume 37, however, can make it difficult or impractical to service the probe 18 and the first and second circuit board assemblies 22, 24, and can substantially increase the weight of the probe 14.

The first and second circuit board assemblies 22, 24 can be mounted using a combination of rigid standoffs 50 and compliant standoffs 52 shown in FIG. 3. In particular, the first and second circuit board assemblies 22, 24 are mounted to the respective housing upper and lower clamshells 30, 32 using the compliant standoffs 52. The first and second circuit board assemblies 22, 24 are mounted to each other using the rigid standoffs 50. Each rigid standoff 50 can be aligned with a corresponding compliant standoff 52, as shown in FIG. 3.

The required rigidity of the compliant standoffs 52 can be specified in terms of the elastic modulus of the standoff material. The actual forces exerted on the circuit boards is governed by the elastic modulus, but also by the ratio of the cross-sectional area to the height of the standoffs 52. For this application, a typical ratio of the cross-sectional area to the height would be 0.004 m, or $\pi$ (pi)*0.25 cm$^2$/0.5 cm. A typical elastic modulus for a compliant standoff is in the range of about 5 MPa to about 50 MPa. A rigid standoff has an elastic modulus that can be substantially higher than this value. For example, a typical value for the elastic modulus of a rigid aluminum standoff is about 70 GPa.

The compliant standoffs 52 can be formed from a compliant material such as soft rubber or silicone RTV. The compliant standoffs 52 can be formed as springs, or other types of compliant devices in the alternative. The compliant standoffs 52 can reduce the peak acceleration of the first and second circuit board assemblies 22, 24 caused by impact loads on the housing 18, in comparison to a rigid mounting arrangement. The compliant standoffs 52 increase the time interval over which the first and second circuit board assemblies 22, 24 are accelerated or decelerated by the impact load. The compliant standoffs 52 can thereby reduce the potential for damage to the first and second circuit board assemblies 22, 24.

The rigid standoffs 50 maintain a fixed spacing between the first and second circuit board assemblies 22, 24. As board-to-board electrical connectors such as the connectors 27 typically require fixed spacing between the interconnected boards, the use of the rigid standoffs 50 may be required in applications where such connectors are used. Conversely, the use of rigid standoffs 50 may not be required in alternative embodiments in which a flexible connection is used between the first and second circuit board assemblies 22, 24.

The rigid standoffs 50 help to transmit impact loads between the upper and lower clamshells 30, 32. In particular, a portion of an impact load applied to the upper clamshell 30 is transmitted to the circuit board 110 of the first circuit board assembly 22 by way of the upper compliant standoffs 52. A portion of the load is then transmitted to the circuit board 110 of the second circuit board assembly 24 by way of the rigid standoffs 50. A portion of the load is subsequently transmitted to the lower clamshell 32 by way of the lower compliant standoffs 50. This arrangement, it is believed, can prevent a substantial portion of the shock load from being absorbed by the first circuit board assembly 22. Instead, the load is distributed between the first and second circuit board assemblies 22, 24 and the lower clamshell 32.

Shock loads applied to the lower clamshell 32 can be transmitted and distributed to the second circuit board assembly 24, the first circuit board assembly 22, and the upper clamshell 30 in a similar manner.

Aligning the rigid standoffs 50 and the compliant standoffs 52, it is believed, also helps to minimize bending of the circuit boards 110 of the first and second circuit board assemblies 22, 24. In particular, aligning each rigid standoff 50 with a corresponding compliant standoff 52 causes the a substantial portion of the load transmitted by the compliant standoff 52 to be transmitted directly to the associated rigid standoff 50 by way of the intervening portion of the circuit board 110. Thus, the load applied by the compliant standoff 52 is substantially aligned with the reactive force exerted by the rigid standoff 50, and localized bending of the circuit board 110 is minimal.

The probe 14 can be equipped with features that minimize the impact loads on the housing 18, and the components located within the housing 18, when the probe 14 is dropped, hit, or otherwise abruptly accelerated.

For example, compliant bumpers 60 can be mounted on the nosepiece 34, as shown in FIGS. 2 and 3. The bumpers 60 can be mounted on the top, bottom, and sides of nosepiece 34, so that the bumpers 60 do not occlude the acoustic window 38, and do not interfere with contact between the acoustic window 38 and the patient. Moreover, compliant cladding 62 can be attached to the exterior surfaces of the upper and lower clamshells 30, 32, to further protect the transducer array 14 from impact loads. Additional compliant bumpers 60 can be mounted on the upper and lower clamshells 30, 32 in lieu of, or in addition to the compliant cladding 62 in alternative embodiments. Additional compliant bumpers 60 and/or additional compliant cladding 62 can be mounted on the battery panel 36 in other alternative embodiments.

The bumpers 60 and the cladding 62 can be formed from a compliant material such as overmolded silicone rubber. For example, SPAPS silicone rubber, available from Bryant Rubber, Harbor City, Calif., can be used in this application. It is believed that the bumpers 60 and the cladding 62 reduce the peak g-forces within the probe 14 when the probe 14 is subjected to an impact load, by increasing the time period over which the probe 14 is accelerated or decelerated in response to the load.

The battery pack 16 can be mated with and removed from the housing 18 by the user, without a need to disassemble the housing 18 or any other components of the probe 14. The ability to remove the battery pack 16 permits the battery pack 16 to be charged without the remainder of the probe 14.

Figure 11:
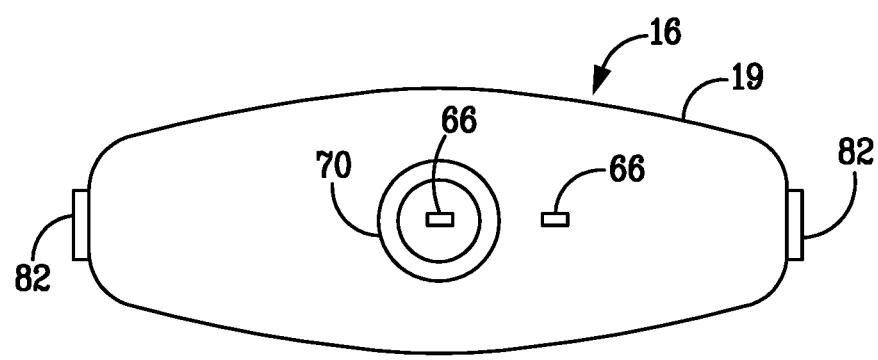
FIG. 11 is a magnified view of the area designated "F" in FIG. 3, viewed from a perspective rotated approximately ninety degrees from the perspective of FIG. 3.
Figure 12:
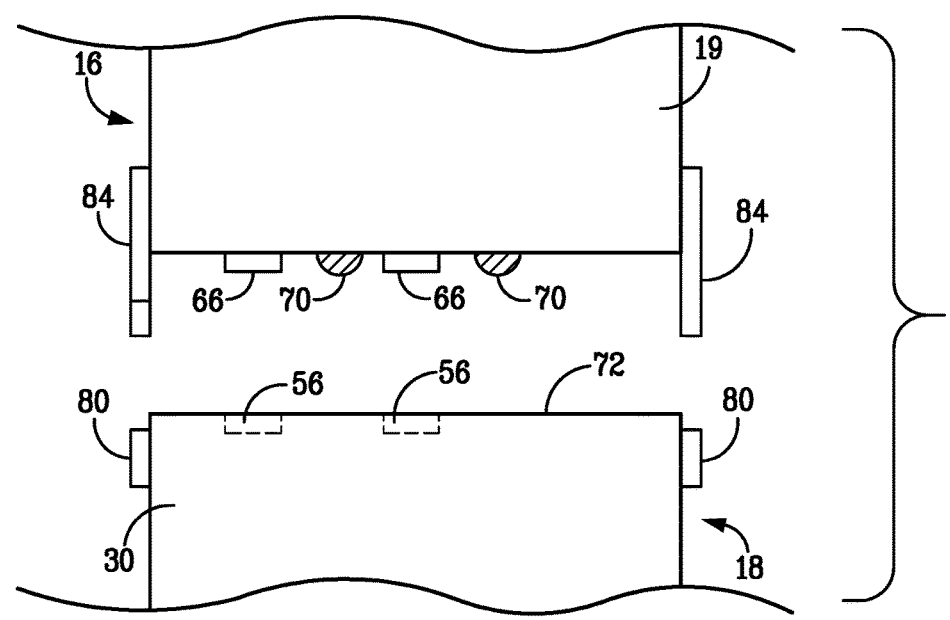
FIG. 12 is a combined, magnified view of the areas designated "E" and "F" in FIG. 3, viewed from a perspective above the probe.

The battery pack 16 includes two contacts 66, as shown in FIGS. 11 and 12. Each contact 66 contacts an associated contact 56 on the battery panel 36 when the battery pack 16 is mated with the housing 18. The contacts 56, 66 establish electrical contact between the battery pack 16 and the first and second circuit board assemblies 22, 24, by way of the leads 54.

The contacts 56, 66 can be formed from materials capable of being exposed to water, ultrasound coupling gel, and other fluids without corroding or otherwise degrading. The contacts 56 can be mounted on the battery panel 36 in a manner that prevents leakage of fluid into the interior volume 37 of the housing 18. The contacts 66 likewise can be mounted on the enclosure 19 of the battery pack 16 in a manner that prevents leakage of fluid into the interior of the battery pack 16. For example, the interface between the contacts 56 and the battery panel 36, and the interface between the contacts 66 and the enclosure 19 can be sealed by casting the contacts 56, 66 into the respective battery panel 36 and enclosure 19 when the battery panel 36 is die cast. Alternatively, the contacts 56, 66 can be cemented into a cavity in the respective battery panel 36 and enclosure 19 with a general-purpose epoxy or other adhesive.

The contacts 56 can be non-deflectable contacts, and are substantially flush with an outer surface 72 of the battery panel 36, as shown in FIG. 12. The contacts 66 can be deflectable contacts. The contacts 66 resiliently deflect when the battery pack 16 is mated with the housing 18, to establish a contact force between the contacts 66 and the contacts 56.

The contacts 56 can be made deflectable, and the contacts 66 can be made non-deflectable in alternative embodiments. The deflectable contacts, however, will likely wear and require replacement prior to the non-deflectable contacts, and are more susceptible to damage during handling than the deflectable contacts. Thus, it is desirable that the contacts 66 be made deflectable since the battery pack 16 is less expensive to replace, and is expected to have a shorter service life than the remainder of the probe 14.

The probe 14 can include features that electrically isolate each mated pair of contacts 56, 66 from the other pair of contacts 56, 66 when the battery pack 16 is mated with the housing 18. For example, an electrically-insulative barrier in the form of a ring-shaped, compressible gasket 70 can be mounted on the battery pack 16, as shown in FIGS. 8, 11, and 12. The gasket 70 can be mounted on the surface 72 of the battery panel 36 in alternative embodiments.

The gasket 70 encircles one of the contacts 66 so that the contacts 66 are separated by the gasket 70, as shown in FIG. 11. The gasket 70 is formed from an electrically-insulative material, and thus forms a barrier that electrically isolates the pair of contacts 56, 66 within the perimeter of the gasket 70 from the pair of contacts 56, 66 located outside of the perimeter when the battery pack 16 is mated with the housing 18.

Ultrasound coupling gel is electrically-conductive. Thus, the battery pack 16 and the housing 18 can be equipped with features that displace ultrasonic coupling gel that may be located at the interface between the gasket 70 and the battery panel 36, to reduce or eliminate the possibility of current flow across the interface.

The battery panel 36 and the battery pack 16, as discussed below, can be equipped with mating features that require the battery pack 16 to be rotated in relation to the housing 18 (or vice versa) when the battery pack 16 is mated with the housing 18. The axis of rotation of the battery pack 16 during mating should pass through or near the center of the gasket 70.

The gasket 70 contacts, and rotates against a the outer surface 72 of the battery panel 36 during mating of the battery pack 16 with the housing 18. The pressure of the gasket 70 against the surface 72, in combination with the rotation of the gasket 70, cause the gasket 70 to displace, or squeeze ultrasound coupling gel or other surface contaminants from the interface between the gasket 70 and the surface 72.

Figure 13A:
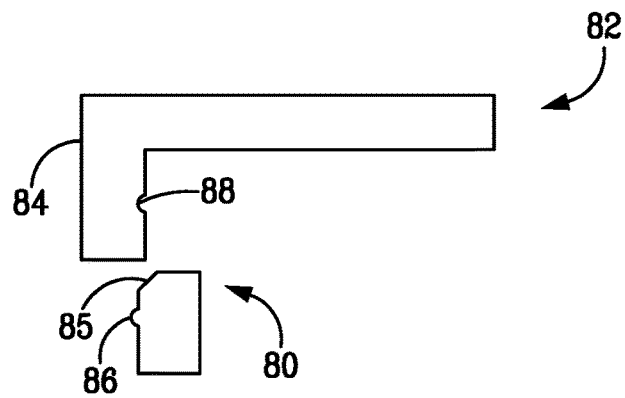
FIGS. 13A-13D are side views depicting mating features on the housing and the battery of the probe shown in FIGS. 1-8A and 10-12, as the battery is mated with the housing.
Figure 13B:
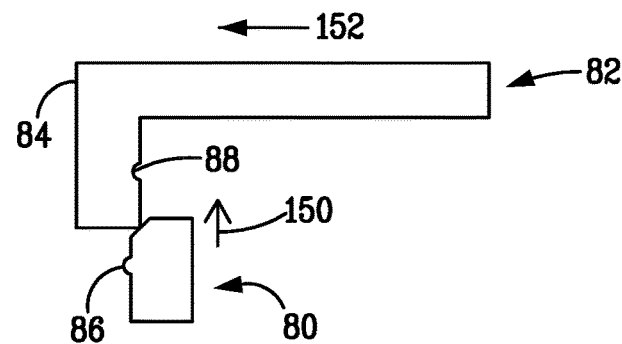
Figure 13C:
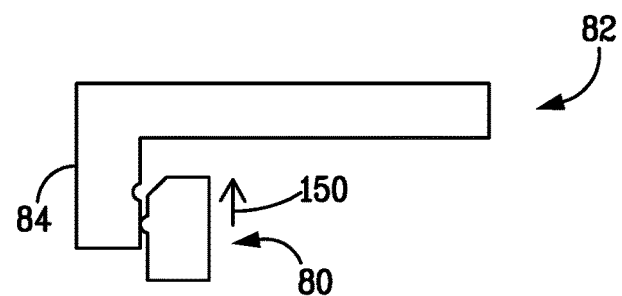
Figure 13D:
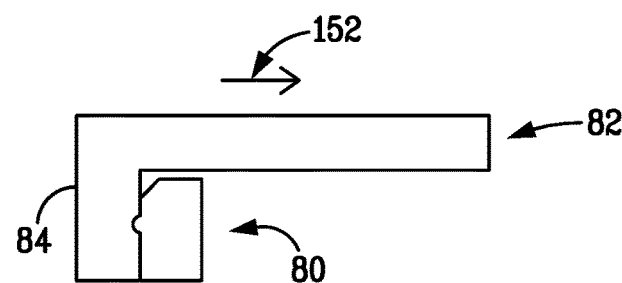

One possible set of mating features for the battery panel 36 and the battery pack 16 is depicted in FIGS. 2 and 10-13D. The mating features are not depicted in other figures, for clarity of illustration. The mating features include two projections 80 formed on opposing sides of the housing 18, and two extensions formed on opposing sides of the enclosure 19 of the battery pack 16. The extensions can be, for example, relatively thin, elongated arms 83 as shown in FIGS. 12-13D. Other configurations for the extensions can be used in alternative embodiments.

The arms 82 each engage an associated projection 80 when the battery pack 16 is mated with the housing 18. The engagement of the arms 82 and the associated projections 80 secures the battery pack 16 to the housing 18. The arms 82 can be formed as part of the housing 18, and the projections 84 can be formed as part of the battery pack 16 in alternative embodiments Each arm 82 has an end portion 84. The end portion 84 of one of the arms 82 faces upward, and the end portion of the other arm 82 faces downward. The downward-facing end portion 84 is shown in FIGS. 2 and 13A-13D. The upward and downward facing end portions 84 necessitate rotation of the battery pack 16 in relation to the housing 18 (or vice versa) during mating of the battery pack 16 and the housing 18.

Each projection 80 can include an inclined surface 85, and a nub, or rounded portion 86 located proximate the inclined surface 85. Each end portion 84 of the arms 82 can have an indentation 88 formed therein.

The battery pack 16 is mated with the housing 18 by aligning the battery pack 16 with the housing 18 so that each projection 80 is offset vertically from its associated arm 82 as shown in FIG. 13A. The battery pack 16 is moved toward the battery panel 36 (or vice versa) until the gasket 70 contacts the surface 72 of the battery pack 16. The arms 82 are sized so that the end portions 84 thereof and the projections 80 are located at the relative positions depicted in FIG. 13A at this point.

Rotation of the battery pack 16 in relation to the housing 18 (or vice versa), in the direction denoted by the arrow 150 in FIG. 13B, causes each end portion 84 to ride up the inclined surface 85 of the associated projection 80, as shown in FIG. 13B. The slope of the inclined surfaces 85 draws the battery pack 16, including the gasket 70, closer to the surface 72 of the battery panel 36, in the direction denoted by the arrow 152 in FIG. 13B. The resulting compression of the gasket 70 against the surface 72 displaces ultrasound coupling gel from the interface between the gasket 70 and the surface 72.

Continued rotation of the battery pack 16, in combination with the resilience of the arms 82, eventually cause each rounded portion 86 of the projections 80 to become disposed in the indentation 88 in the associated end portion 84, as depicted in FIG. 13D. The positioning of the projections 80 in the indentations 88 permits the battery pack 16 to back away slightly from the battery panel 36, in the direction denoted by the arrow 152 in FIG. 13D, thereby relieving some of the pressure on the gasket 70. In other words, the mechanical interaction between the arms 82 and the projections 80 causes the gasket 70 to be compressed beyond its final state of compression during mating of the battery pack 16 and the housing 18.

Partially relieving the pressure on the gasket 70 at the end of the mating process relieves some of the pressure on the ultrasound coupling gel that has been squeezed inward within the perimeter of the gasket 70. Reducing the pressure on the ultrasound coupling gel reduces the potential for the gel to continue to leak outwardly, past the gasket 70. Such leakage can create an unintended conduction path between the electrical contacts 56, 66.

In applications in which more than two sets of battery contacts 56, 66 are used, additional gaskets such as the gasket 70 can be positioned between each set of contacts 56, 66.

The battery pack 16 may be immersed in or otherwise in contact with ultrasound coupling gel, water, or other electrically-conductive fluids when the battery pack 16 is in an un-mated condition. Thus, the battery pack 16 can include switching features that prevent voltage from being present at the contacts 66 when the battery pack 16 is not mated with the housing 18 or the charging station 106, to prevent unintentional discharge of the battery 17 due to contact with such fluids.

For example, the battery pack 16 can include a switching feature in the form of a relay, such as a "form A" (normally open) reed relay 92 depicted in FIGS. 7 and 8. The relay 92 is electrically connected in series with one of the contacts 66 of the battery pack 16 and the battery 17, so that the relay 92 can interrupt electrical contact between the contact 66 and the battery 17. A magnet 96 can be mounted on an interior surface of the battery panel 36, as shown in FIG. 8. The magnet 96 can be positioned so that its magnetic field draws a switch 92a of the relay 92 into its closed position when the battery pack 16 is mated with the housing 18, thereby establishing electrical contact between the battery 17 and the contact 66. The charging station 106 for the battery pack 16 can include a similar feature.

De-mating the battery pack 16 from the housing 18 or the charging station 106 removes the relay 92 from the magnetic field generated by the magnet 96, thereby permitting the switch 92a to return to its open position. The return of the switch 92a to its open position breaks electrical contact between the battery 17 and the contact 66, thereby preventing the battery 17 from discharging by way of the contact 66.

One or both of the battery pack 16 and the battery panel 36 can be equipped with pieces of magnetically-permeable material (not shown) that focus, or concentrate the magnetic flux of the magnet 96 toward the relay 92.

The use of the magnet 96 and the relay 92 obviates the need to provide penetrations in the enclosure 19 of the battery pack 16, or the battery panel 36. This configuration therefore does not introduce the potential for infiltration of fluids into interior volume 37 of the probe 14, or into the interior of the enclosure 19 of the battery pack 16.

Figure 9:
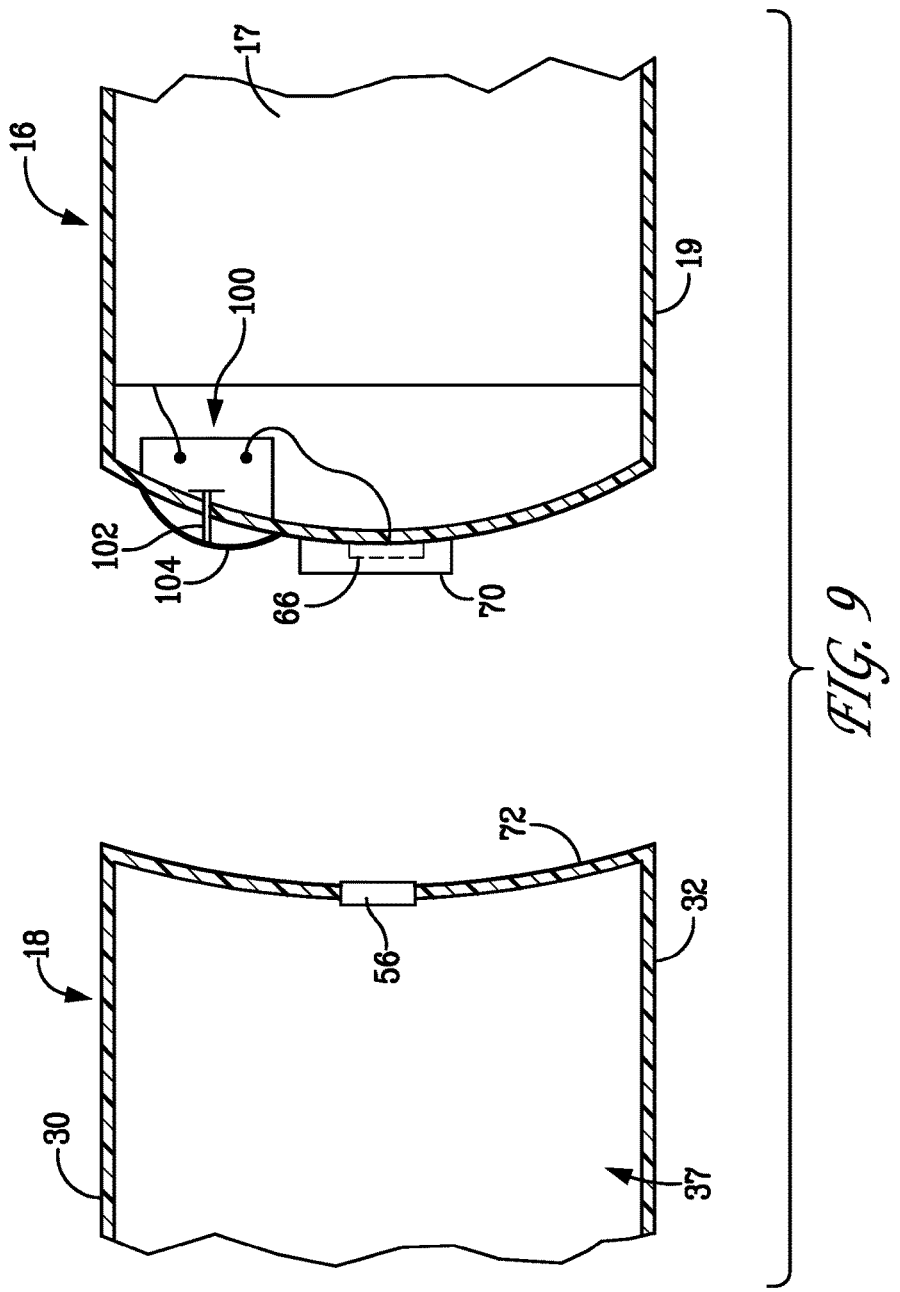
FIG. 9 is a view taken from the perspective of FIG. 8A, depicting another alternative embodiment of the probe shown in FIGS. 1-8A.
Figure 10:
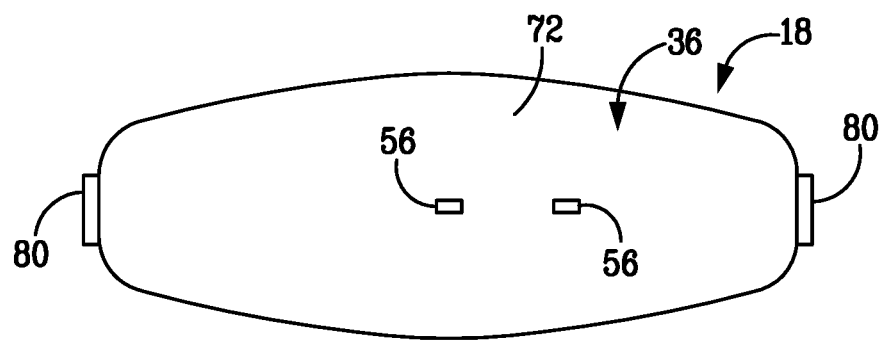
FIG. 10 is a magnified view of the area designated "E" in FIG. 3, viewed from a perspective rotated approximately ninety degrees from the perspective of FIG. 3.

Alternatively, the battery pack 16 can be equipped with a switch 100, as shown in FIG. 9. The switch 100 is electrically connected in series with one of the contacts 66 of the battery pack 16 and the battery 17, so that the switch 100 can interrupt electrical contact between the contact 66 and the battery 17. The switch 100 can be actuated by a movable contact 102 thereof. The contact 102 is biased outwardly, i.e., in a direction away from the battery pack 16, toward its open position, by a suitable means such as a spring (not shown). The contact 102 can be covered by a flexible membrane 104. The outer periphery of the membrane 104 is bonded to or encased by the enclosure 19, to prevent fluids from entering the interior of the enclosure 19 by way of the interface between the membrane 104 and the enclosure 19.

The surface 72 of the battery panel 36, or a surface on the charging station 106 contacts the membrane 104 as the battery pack 16 is mated with the battery panel 36 or the charging station 106. The membrane 104 can flex inwardly, i.e., toward the battery pack 16, so that the surface 72 urges the contact 102 toward its closed position as the battery pack 16 and the battery panel 36 or charging station 106 are mated. The switch 100, upon reaching its closed position, places the battery 17 in electrical contact with the contact 66.

The switch 100 can be used without the membrane 104 in alternative embodiments. A suitable sealing means, such as a TEFLON seal, should be provided between the contact 102 and the enclosure 19 is such embodiments, to prevent infiltration of fluids into the enclosure 19 of the battery pack 16.

In other alternative embodiments, the battery pack 16 can include an electrical circuit 94, and a switch in the form of a hall effect sensor 93 connected in series with one of the contacts 66 and the battery 17, as shown in FIGS. 8B and 8C. The electrical circuit is configured to activate the switch when the electrical circuit determines that the battery pack has been mated to the probe 18 or a charging station 106. The hall effect sensor 93 is used in a manner similar to the reed relay 92. In particular, when the hall effect sensor 93 senses a magnetic field in the proximity thereof, the electrical circuit 94 turns on the MOSFET 95. Turning on the MOSFET 95 completes a circuit from the battery to the contacts 66, allowing current to flow into or out of the battery 17. It is necessary to permit current to flow into or out of the battery 17 so that the battery 17 can be charged, and used as a power source.

The battery pack 16, upon reaching a charge state unsuitable for continued use, can be replaced with a charged battery pack 16. The change-out of the battery pack 16 can be performed quickly and easily by the user. One or more battery packs 16 can be continually charged on a charging station, such as the charging station 106 of the base unit 12 as depicted in FIG. 1, so that a recharged battery pack 16 is available when needed. The probe 14 therefore can be used on a substantially continuous basis. The continuous availability of the probe 14 can eliminate the need to substantially interrupt or delay a medical procedure to accommodate charging of the probe 14.

Alternatively, it is possible to make the battery pack 16 a single-use battery pack, so that the charging station 106 is not needed. The useful life of a single use version of the battery pack 16, however, would need to be relatively long, e.g., several hours, to make the use of the single-use battery pack 16 feasible.

In other embodiments, a stand-alone charging station can be used in addition to, or in lieu of the charging station 106 on the base unit 12. A stand-alone charging station can be connected continuously to an electrical power outlet or other source of electrical power, so that the charging station maintains a supply of fully charged battery packs 16 that are ready for use with the probe 14 or probes 14 that are being used at a particular time.

Moreover, the ability to charge the battery pack 16 without the remainder of the probe 14 can eliminate the need to place the charging infrastructure, e.g., inductive pickups, electrical contacts, supervisory circuitry, and battery charger circuits, in the probe 14. The use of a removable battery pack such as the battery pack 16 can thus make the probe 14 lighter, more compact, and less complex than a comparable probe having a non-removable battery pack.

The first or second circuit board assemblies 22, 24 of the probe 14 can be configured to monitor the charge state of the battery pack 16 in use on the probe 14. The charge-state information can be transmitted to the base unit 12 and displayed on the monitor 126.

Displaying the charge-state information on the monitor 126 can eliminate the need for the user to look away from the monitor 126, and the ultrasound image thereon, when checking the charge state of the battery 17. Moreover, displaying the charge-state information on the base unit 12, instead of on the probe 14, eliminates the need to utilize power from the battery 17 to operate such a display.

Alternative embodiments of the probe 14 can include an internal, non-removable battery in lieu of the battery pack 16. An example of probe 14a having an internal, non-removable battery pack 138 is depicted in FIGS. 15A-15D. Components of the probe 14a that are substantially similar or identical to those of the probe 14 are denoted in the figures by identical reference characters.

FIG. 15A depicts the probe 14a being inserted into a charging stand 144. The acoustic window 38 is shown at the top of the probe 14a for reference. The probe 14a is inserted into the charging stand 144 in a direction denoted by the arrow 156. The charging stand 144, like the battery charging station 106, can be integrated into the base unit 12 or, alternatively, can be constructed as a stand alone unit.

Alternative embodiments of the charging stand 144 can include multiple charging ports. Each charging port can be independently active, so that the charging ports can maintain the charge of multiple probes 14 simultaneously.

The probe 14a can have exposed electrical charging contacts 130 that are electrically connected to the battery pack 138. The charging contacts 130 come to rest against mating contacts 145 in the charging stand 144 when the probe 14a is inserted into the charging stand 144. Battery charging circuitry within the charging stand 144 can supply electric current to the battery pack 138 to recharge the battery pack 138. The charging contacts 130 can be positioned on the bottom of the probe 14a as in FIG. 15B.

Alternatively, the charging contacts 130 can be positioned on the sides of the probe 14a, as in FIG. 15C. A contact wiper 146 can be employed in this embodiment to remove some or most of any contaminants that may be present on or around battery charging contacts 130. The wiper 146 can be made of EPDM rubber or other suitable material that is highly flexible and resilient. The wiper 146 can completely encircle a probe entry port 147 of the charging station 144, to wipe the entire circumference of the body of the probe 14a. Alternatively, the wiper 146 can be configured to wipe only limited areas around the battery charging contacts 130 or elsewhere on the body of the probe 14a. The wiper 146 may not completely remove any contaminating materials; however, the wiper only needs to provide a conductivity break in any contaminating materials so that there is no conductivity path from one mated pair of charging contacts 130, 145 to the other.

Since the batteries of the probe 14a are non-removable, the entire probe 14a or a substantial portion of the probe 14a can be inserted into the charging stand 144. Charging current is carried from the charging station 144, through the mated pairs of contacts 145, 130, and to the non-removable battery pack 138, where current recharges the battery pack 138.

Figure 14A:
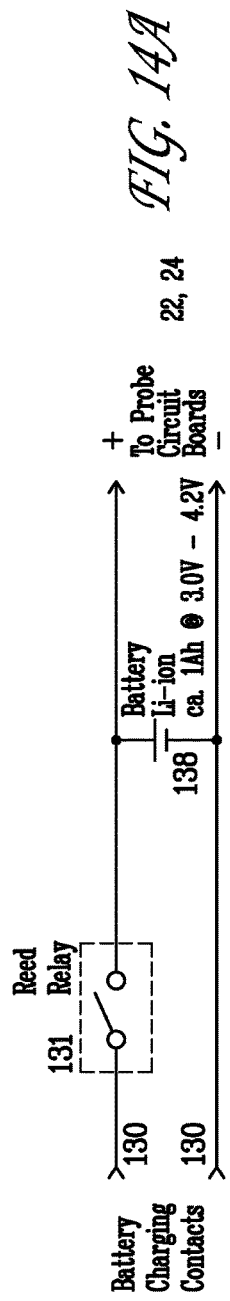
FIGS. 14A-14D depict four different electrical circuits for use with the probe shown in FIGS. 15A and 15B, wherein the electrical circuits electrically isolate battery charging contacts of the probe from internal circuitry of the probe when the probe is not located in the charging stand depicted in FIGS. 15A and 15B.
Figure 14B:
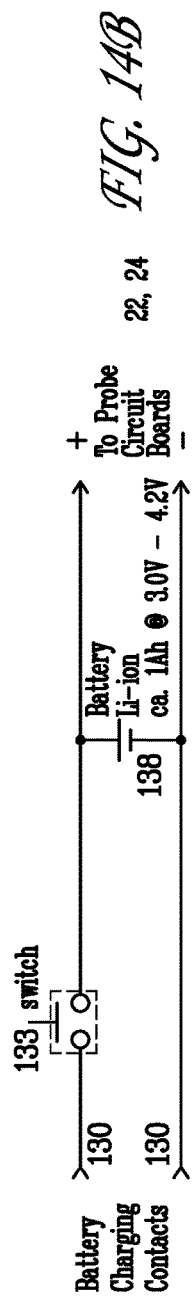

The probe 14a can be equipped with switching features, such as a reed relay 131 or a switch 133, that prevent discharge of the battery pack 138 when the probe 14a is not located in the charging station 144 and one or more conductive materials, such as ultrasound coupling gel, are in contact with the exposed charging contacts 130. The reed relay 131 and the switch 133 are depicted in FIGS. 14A and 14B, respectively.

The reed relay 131 or the switch 133 can be configured to electrically connect the battery pack 138 to one of the charging contacts 130 in the manner discussed above in relation to the respective reed relay 92 and switch 100 described above in relation to the battery pack 16 of the probe 14. For embodiments equipped with the reed relay 92, the charging stand 144 can be equipped with a magnet (not shown) that is oriented so that the magnet closes the reed relay 92 when the probe 14a is fully inserted into the charging stand 144.

In other alternative embodiments, the probe 14a can include an electrical circuit, and a switch connected in series with one of the charging contacts 130 and the battery pack 138. The electrical circuit is configured to activate the switch when the electrical circuit determines that the battery pack 138 has been mated to the charging stand 144. The electrical circuit and the switch can be substantially similar or identical to the electrical circuit 94 and the hall effect sensor 93 discussed above.

Current needs to flow in only one direction through the charging contacts 130 of the non-removable battery pack 138, i.e., current needs to flow into, but not out of the probe 14a by way of the charging contacts 130. The probe 14a can therefore be equipped with features, such as a Schottky diode 132, located in series with one of the charging contacts, to prevent reverse flow of current through the charging contacts. A suitable Schottky diode can be obtained, for example, from Diodes, Inc., of Westlake Village, Calif., as the model B340 diode.

Alternatively, a MOSFET 136 or another type of semiconductor switching device can be used to interrupt electrical contact between one or more of the charging contacts and the battery when the battery is not being charged. In both of these diagrams, a capacitor 137 and a diode 139 act as an input protection circuit, preventing reverse voltages and fast rise time voltages on the charging contacts 130. This will render the internal circuitry less vulnerable to ESD and other adverse input voltages and currents.

Figure 14C:
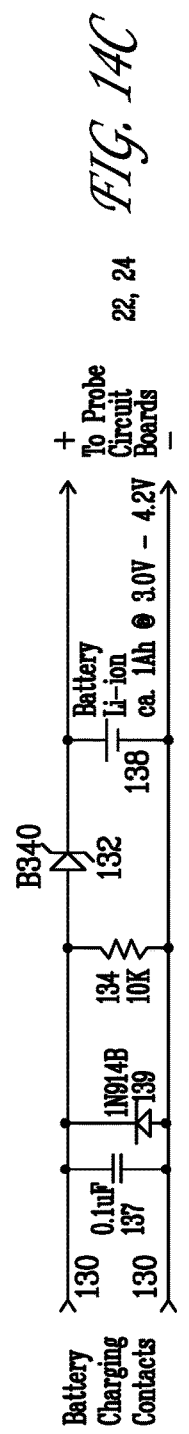
Figure 14D:
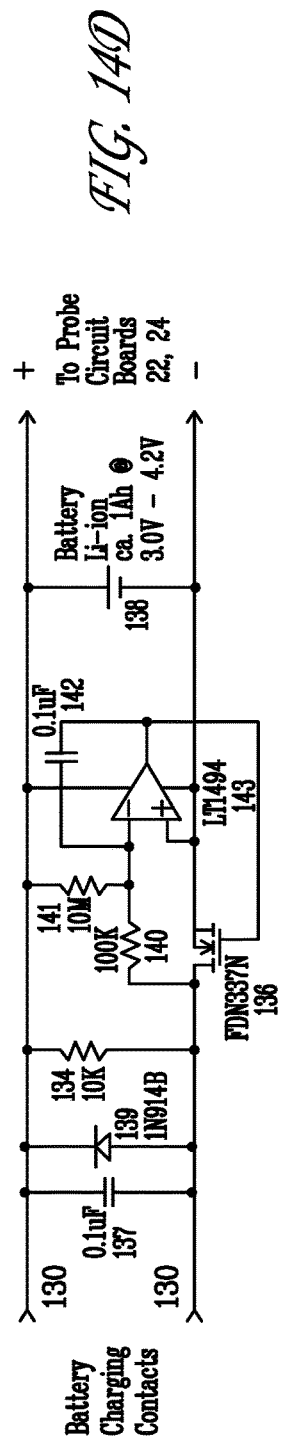

As shown in FIGS. 14C and 14D, the input resistor 134 holds the input potential across the charging contacts 130 to zero whenever the probe 14a is not connected to a charging station. Thus, any conductivity across the charging contacts 130 due to the presence of a conductive material bridging the charging contacts 130 would not present a problem, because no current would flow through the conductive material. Once the probe 14a is connected to the charging station 144, as long as this shunt current path does not carry an excessive amount of current, any current flowing through the shunt current path should not present a problem for the charging circuitry within station 144, and can be considered negligible.

Alternatively, the charging circuitry in the charging station 144 can be configured to test for a shunt current before the commencement of the charging cycle. The charging circuitry can perform this test by providing a small potential across the mated pairs of charging contacts 130, 145, and sensing the resulting current flow. Both of the circuits depicted in FIGS. 14C and 14D provide a 10K ohm shunt resistance if the charging voltage is less than the voltage across the terminals of the battery pack 138. If the shunt current through any contaminant path between the mated pairs of charging contacts 130, 145 is excessive, the charging stand 144 can be configured to display a fault light or message that alerts the user to clean the probe 14a or the charging stand 144 of any conductive materials. Once the shunt path is so reduced so that the current therethrough is negligible, the charging circuitry would commence the charging cycle.

During initial charging of the battery pack 138, the power dissipation in the diode 132 could be on the order of 0.4 W. Some amount of heat sinking therefore is required to avoid overheating the diode 132. Moreover, in embodiments of the battery pack 18 that comprise a lithium-ion battery, the final-state charging voltage is critical, and needs to be set within a few tens of millivolts to accurately finish the charge cycle and assure a full charge. Because the voltage drop across the diode 132 is not known a-priori to this level of accuracy, the actual voltage across the terminals of the of battery pack 138 needs to be determined in a manner that does not rely on the measured voltage drop across the diode 132.

The circuit depicted in FIG. 14D addresses the above needs through the use of a MOSFET 136 such as use of a low-threshold type MOSFET available from Fairchild Semiconductor of South Portland, Me. as the model FDN337N MOSFET. This MOSFET has a guaranteed "on" resistance of Rds(on)<0.08 Ohm at a gate voltage of 2.5V. Thus, at typical charging currents of C/2 to C (0.5 A to 1 A for a 1 Ah battery such as battery pack 138), the power dissipation in the MOSFET 136 will be negligible, i.e., <80 mW.

Moreover, the circuit of FIG. 14D provides a relatively low voltage drop across the pass element, MOSFET 136, so that the final-stage charging voltage can be set accurately. As the final charge voltage is reached, the charging current in the MOSFET 136 drops, and the voltage across the terminals of battery pack 138, subsequently referred to as $V_{battery}$, is known to a relatively high accuracy due to the diminishing I*R drop across the MOSFET 136. At low charging currents, such as those near the end of a charging cycle, the product of the MOSFET 136 Rds(on) and the charge current through contacts 130 is less than 1% of the voltage across the charging contacts 130, subsequently referred to as $V_{charger}$. The voltage across the terminals of the battery pack 138 can be computed with a relatively high degree of accuracy as $V_{battery}=0.99*V_{charger}$.

The self-discharge of typical Li-ion batteries is 5% per month. For a 1 Ah battery pack such as 138, this represents an equivalent self-discharge current of about 70 uA. The op-amp 143 in FIG. 14D consumes only 1.5 uA of power supply current, and thus represents a negligible additional power drain on the battery pack 138. Therefore, there is no need to shut the op-amp 143 off. The op-amp 143 senses the voltage across the MOSFET 136, and drives its gate to try to force the voltage drop across it to 1% of the battery terminal voltage. At high charge currents, this will not be possible, due to the Rds(on) of MOSFET 136, so the output of the op-amp 143 will saturate against its positive rail, and the MOSFET 136 will be driven so as to provide as low a drop as possible. When the charging current drops sufficiently, the op-amp 143 will move into its linear operating range and it will regulate the gate drive to the MOSFET 136 to provide a voltage drop through MOSFET 136 of 1% of the battery terminal voltage.

A fuel cell can be used in lieu of a rechargeable battery in other alternative embodiments. The fuel cell can use a suitable fuel such as hydrogen or methanol. The fuel cell can be configured to be removable by the user, so that a depleted fuel cell can quickly be replaced with another fuel cell that has been filled with fuel. Alternatively, the fuel cell can be configured to be re-filled quickly, thereby obviating the need for the fuel cell to be removable.

The probe 14 can undergo leak testing before being provided to the user, to verify that the probe 14 is properly sealed. Leak testing can be conducted by introducing air or some other gas into the interior volume 37 of the housing 18, by way of a small through hole formed in the housing 18. The pressure of the gas within the probe can be monitored for a predetermined time period. A stable, i.e., substantially constant, pressure reading can be considered an indication that the probe 14 is properly sealed. Conversely, a decrease in pressure over time can be considered an indication that a leak is present at one or more locations in the probe 14.

Alternatively, the interior volume 37 of the probe 14 can be pressurized, and leaks can be detected by directly observing escaping gas. For example, the probe 14 can be immersed in a liquid so that bubbles from at the site of leakage can be observed. Alternatively, the exterior of the probe 14 can be coated with a simple soap solution so that bubbles from the site of the leakage can be observed.

Alternatively, a tracer gas can be introduced into the probe 14 through the opening formed in the housing 18. The tracer gas can be detected upon escaping from the probe 14 due to the presence of a leak, thereby providing an indication of the location of the leak. The use of the relatively expensive tracer gas may not be cost effective, however, in applications where the corrective action to be taken includes disassembling and resealing the entire housing 18 to eliminate the leak.

Alternatively, a vacuum can be applied to interior volume 37 of the housing 18 by way of the opening formed in the housing 18. The vacuum can be monitored, and a decrease in the vacuum level, i.e., the inability to maintain a vacuum in the interior volume 37, can be interpreted as an indication that a leak is present at one or more locations in the probe 14.

The hole through which the gas or vacuum is introduced can be closed and sealed once the probe 14 has been found to be free of leaks. The hole can be closed and sealed using, for example, adhesive, a plug that may or may not be permanently cemented into the hole, or other suitable means.

The interior volume 37 of the probe 14 can be filled with an inert gas before the hole is closed and sealed, to inhibit or prevent surface oxidation of metallic components, such as the contacts of electrical connectors, located within the housing 18.

A second hole can be formed in the housing 18, to permit the air displaced by the inert gas to escape from the interior volume 37 as the inert gas is introduced. The holes can be formed in an inconspicuous location on the housing. For example, the holes can be formed through the surface 72 of the battery panel 36, which is normally covered when the battery pack 16 is mated with the remainder of the housing 18.

Other methods for checking the watertight integrity of the probe can be used. For example, if the probe is a wired, rather than a wireless probe, the nosepiece 34 and some or all of the backshell 42 can be immersed in an electrically-conductive liquid, and a DC or AC voltage applied between the conductors of the probe's cable and the liquid. The absence of DC current flow, or the absence of AC current flow beyond the amount expected due to the capacitance between the internal circuitry of the probe 14 and the liquid, can be interpreted as a indication that the watertight integrity of the probe is satisfactory.

If the probe is a wireless probe, other means must be employed to carry out an equivalent test. For a wireless probe with a removable battery pack, such as the probe 14, an adapter can be provided. The adapter attaches to the probe 14 at the site where the battery pack 16 normally attaches. The adapter facilitates attachment of the DC or AC potential used for a current leakage test to be attached to the internal circuitry of the probe 14, to allow the probe 14 to be tested in the same manner as a wired probe.

If the probe has an internal, non-removable battery such as the probe 14a, an adapter can provided. The adapter can attach to the probe 14a, and contacts the battery charging contacts 130 to provide a connection to the circuitry inside the probe 14a. A current leakage test can then be carried out in the manner described above for a wired probe.

Alternatively, a hole can be provided in housing 18 as described above. One or more conductors could be passed through the hole. The conductors can be connected to the internal circuitry of the probe 14, 14a. A current leakage test can then be carried out in the manner described above for a wired probe. Once the current leakage test has been successfully completed, the hole can be closed and sealed to isolate the interior volume 37 from the environment around the probe 14, 14a.

As shown in FIG. 3, a large portion of the internal volume 37 of the probe 14 can be filled with air or other gas. Thus, when testing the watertight integrity of the probe 14 using an immersion test, a substantial amount of liquid may enter the interior volume 37 of the probe 14 before a conductivity path is established between the liquid around the probe 14 and the internal circuitry of the probe 14. Thus, for the test to be effective at identifying leaks, the probe 14 may need to immersed in the liquid for a relatively long period. Also, having a conductive liquid in and around the internal circuitry of the probe 14 can potentially damage the circuitry and render the probe 14 unserviceable.

Thus, when conducting an immersion test, it is desirable to quickly detect leaks before a substantial amount of liquid incursion in the interior volume 37 can occur. A relatively quick leak check can be facilitated by providing a conductive path from one of the conductors of the circuit boards, preferably "ground" or the reference potential of the circuit boards, to the inner walls of the nosepiece 34, the upper and lower clamshells 30, 32, and/or the battery panel 36, and especially in areas around and along the joints therebetween. Liquid leaking into the interior volume 37 will quickly come into contact with these conductors and provide a current conduction path indicative of a leak, before there is substantial liquid incursion.

A conductive path can be provided by different means. For example, a conductive coating 168 can be applied to the inner surfaces of the nosepiece 34, the upper and lower clamshells 30, 32, and/or the battery panel 36 by painting, spraying, or sputtering. For example, a suitable coating is SPI#5001-AB Silver Paint, available from SPI Supplies of West Chester, Pa. This material is a silver-loaded paint that, upon the evaporation of the solvent carrier, leaves a highly conductive film of silver metal on the coated surface. A portion of the coating 168 is depicted in phantom in FIG. 3.

A conductor can be provided between the conductive coating and a reference node or nodes of the first and/or second circuit board assemblies 22, 24. The conductor can be one or more wires from the circuit boards 22, 24 to one or more of the nosepiece 34, upper and lower clamshells 30, 32, and battery panel 36. The wires can be attached to the circuit boards 110 of the first and/or second circuit board assemblies 22, 24 with conductive epoxy, such as SPI#05067-AB conductive epoxy, available from SPI Supplies of West Chester, Pa. The wires can be attached to the circuit boards 110 in the manner described above in relation to the lead 54.

An electrically-conductive shield 170 connected to one or more reference nodes on the first and/or second circuit board assemblies 22, 24 can be used as the conductive path in alternative embodiments. The shield 170 be attached to the first and/or second circuit boards 22, 24 before the first and/or second circuit boards 22, 24 are mounted within the housing 18, thus making it relatively easy to install the shield. A portion of the shield 170 is depicted in phantom in FIG. 3.

The shield 170 also provide EMI control for the circuitry on the first and/or second circuit board assemblies 22, 24. For example, the shield 170 lessen the sensitivity of the TGC receiver 114 to impinging electromagnetic fields that can potentially corrupt the low-amplitude echo signals. The shield 170 also limit radiated electromagnetic fields from the circuitry on the first and/or second circuit board assemblies 22, 24 to the surrounding environment, or to other circuitry within the probe 14 itself.

In providing a wired interface, or cable assembly, between a probe and its base unit, it can be beneficial to minimize the number of conductors in the cable assembly. This can reduce the cost and size of the cable assembly, and can improve the ergonomics of the probe. If the cost of the cable assembly can be made relatively low, it can be feasible to make the cable assembly a sterilized, disposable, single-use item, such as the cable assembly 149 depicted in FIG. 16A.

A new, sterile cable assembly 149 can be used each time the user begins a sterile procedure with the ultrasound transducer 14*b*. The sheathing procedure for the probe 14*b* is relatively simple, because the sheath needs to cover only the probe 14*b*, and not the cable assembly 149.

The cable assembly 149 can be used in conjunction with a probe 14*b* depicted in FIG. 16A. The cable assembly 149 comprises a cable 147, and a first connector 148 electrically and mechanically connected to a first end of the cable 147. The first connector 148 can mate with the probe 14*b*, at an end of the probe 14*b* opposite the acoustic window. The cable assembly 149 also includes a second connector 151 electrically and mechanically connected to a second end of the cable 147. The second connector 151 can mate with a base unit such as the base unit 12. The first connector 148 and the second connector 151 can be identical, so that the cable assembly 149 is omni-directional, i.e., so that either end of the cable assembly 149 can be connected to the probe 14 and the base unit 12.

The cable assembly 149 is detachable or removable at both ends thereof, i.e., the first connector 148 can be disconnected from the probe 14*b*, and the second connector 151 can be disconnected from the base unit 12 without damaging or otherwise rendering non-reusable the probe 14*b*, the base unit 12, and/or the first or second connectors 148, 151. The probe 14*b*, the base unit 12, and the first and second connectors 148, 151 can be equipped with suitable mating features that secure the first and second connectors 148, 151 to the respective probe 14*b* and base unit 12 while facilitating removal of the first and second connectors 148, 151 as noted.

The first connector 148 includes two electrical contacts 157, and a housing 167. Each contact 157 contacts an associated electrical contact 156 on the probe 14*b* when the first connector 148 is mated with the probe 14*b*, to establish electrical contact between the probe 14*b* and the base unit 12. The contacts 156, 157 are shown in FIGS. 16A and 16B, respectively.

An electrically-insulative barrier, such as the ring-shaped, compressible gasket 70 described above in relation to the probe 14, can be mounted on the housing 167 at a mating face 161 of the first connector 148, as shown in FIG. 16A. The gasket 70 can be mounted on a mating face 160 of the probe 14*b* in the alternative. The second connector 151 can also be equipped with one of the gaskets 70 to permit the cable assembly 149 to be used in an omni-directional manner, i.e., to permit the second connector 151 to be mated with the probe 14.

The gasket 70 encircles one of the contacts 157, and is pressed against the mating face 160 of the probe 14*b* when the probe 14*b* and the first connector 148 are mated. The gasket 70 can displace ultrasound coupling gel or other contaminants from the mating face 160, thereby providing electrical isolation between the mated pairs of contacts 156, 157 in the manner described above in relation to the contacts 56, 66 of the probe 14.

The mating face 160 and the contacts 56 of the probe 14 can be replicated on a panel of the base unit 12, so that the first connector 148 of the cable assembly 149 can also be mated with the base unit 12 in the same manner as the first connector 148 is mated with the probe 14.

The probe 14*b* can include two or more of the arms 82 described above in connection with the probe 14, as shown in FIG. 16D. The first connector 148 can be equipped with an equal number of the projections 80 also described above in connection with the battery panel 36. The arms 82 and the projections 80 act collectively to pull and hold together the probe 14*b* and the first connector 148, in the manner described above in relation to the battery pack 16 and the battery panel 36 of the probe 14*b*. The use of the arms 82 and the projections 80 to fasten the first connector 148 to the probe 14*b* is described for exemplary purposes only. Other fastening means, such as latches or to fasteners, can be used in the alternative.

The first and second connectors 148, 151 can be configured with more than two of the contacts 157 each, and the probe 14*b* can be configured with more than two of the contacts 156. As described above in relation to the probe 14, additional compliant gaskets 70 can be provided to facilitate isolation of the additional pairs of contacts 156, 157, as shown in FIG. 16C. The multiple compliant gaskets 70 can be concentric, so that the same rotational engagement motion causes all of the gaskets 70 to simultaneously displace ultrasound coupling gel or other contaminants from the mating face 160 of the probe 14*b*.

Minimizing the number of conductors in the cable 147 can help minimize the number of contacts 156, 157 required to establish electrical contact between the probe 14*b* and the base unit 12, and can reduce the cost, size, and weight of the cable 147. It is possible to use a single pair of conductors plus ground (three wires) to implement the three functional requirements of the wired interface: carrying power from the base unit 12 to the probe 14*b*; carrying control information from the base unit 12 to the probe 14*b*; and carrying control, status and image information from the probe 14*b* to the base unit 12.

The base unit 12 and the probe 14*b* can be configured to communicate with each other alternately, i.e., on a non-simultaneous basis. Two-way communications between the base unit 12 and the probe 14*b* can be accommodated over a single communication path, i.e., over one wire pair, using this configuration, due to the absence of two-way data communication.

Alternatively, simultaneous two-way communications over a single conductor can be facilitated using techniques such as time, frequency, or other types of multiplexing, directional couplers that isolate the transmitted date from the received data, etc.

The base unit 12 sends configuration information to the probe 14*b*, to place the probe 14 into the proper mode of operation. The probe 14*b* sends image data and some status and control information back to the base unit 12. It is possible to provide a break in the signal flow between the probe 14b and the base unit 12 to permit the base unit 12 to alternately send control information, such as information that causes the mode of operation of the probe 14b to change in response to a user input, to the probe 14b. This time multiplexing can take advantage of the nature of the operational characteristics the probe 14, in which acoustic transmit events are followed by echo data collection. The data sets resulting from a single acoustic transmit event are the natural data segmentation in the probe-to-base unit communications that can provide this time segmentation.

In the case of a synthetic-focus data gathering scheme, the acoustic transmit is from a single transducer element, or a group of elements fired simultaneously to create a diverging wavefront. In the case of a conventional beam-based system, the acoustic transmit event is a simultaneous firing of a group of elements to create a steered and/or focused transmit beam. In both of these cases, the acoustic transmit event is followed by echo signal data collection from multiple transducer elements. The resulting echo data set may or may not be beamformed, and then sent to the base unit 12 for further processing and display.

In the case of an analog receive beamformer system, the acoustic transmit event is a steered and/or focused transmit beam, and the resulting received echo is analog-beamformed. The beamformed analog signal is sent over the cable assembly 149 to the base unit 12 to be digitized, processed, and displayed. In all cases, after the receive echo information is sent to the base unit 12, the communications link is available to send data from the base unit 12 to the probe 14b. Once this data is sent, the probe 14b again takes control of the link to send another echo signal or data set.

Figure 17:
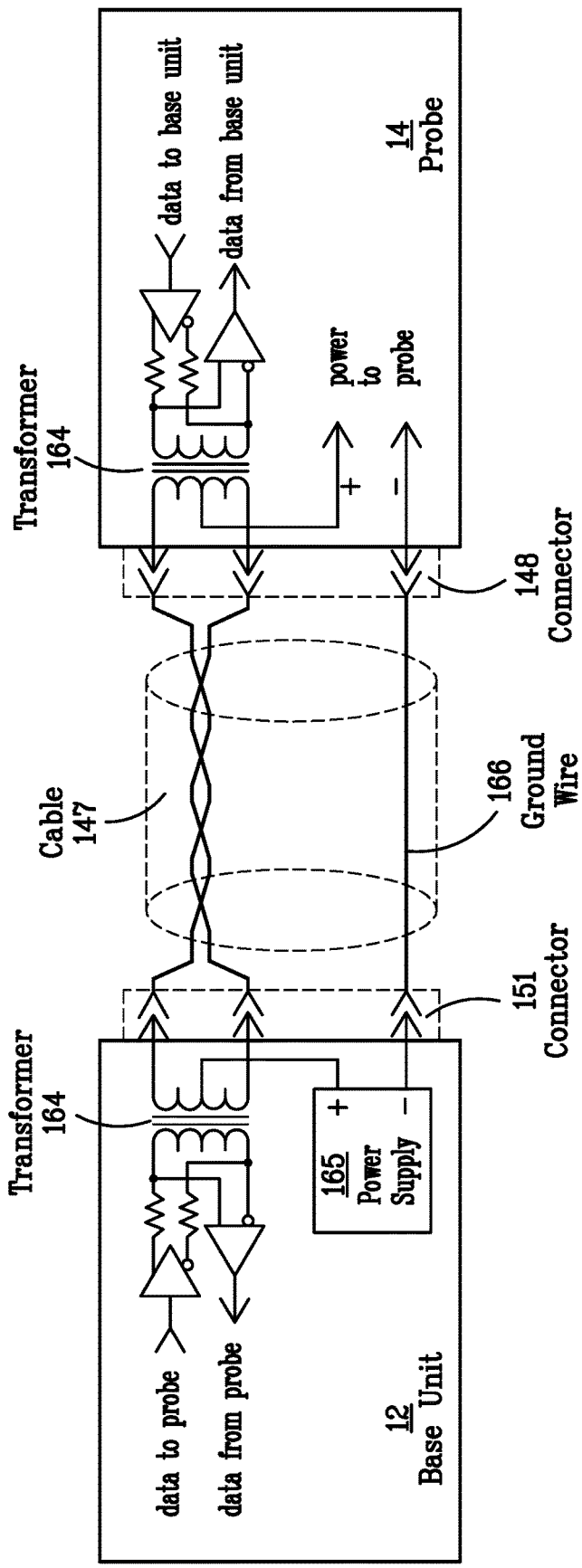
FIG. 17 depicts circuitry of the probe and the cable assembly shown in FIGS. 16A-16C, wherein the circuitry facilitates data communications and power transfer between the probe and a base unit.

In addition to providing two-way communication between base unit 12 and the probe 14, it is also necessary to provide power to the probe 14. It is also desirable to provide a differential communications signal between the base unit 12 and the probe 14 to provide immunity to radio-frequency interference and relatively low radiated emissions. Both of these features can be provided by using center-tapped transformers on both ends of the cable to feed in the power as a common-mode signal on a differential data path, as shown in FIG. 17. A power supply 165 in the base unit 12 can provide power through the center tap of the data line transformer 164. The return power supply current returns through a separate ground wire 166. Alternatively, power and data communications can be provided through a two-wire interface. The components needed to isolate the power and data signals from each other, however, would be more bulky than the small signal transformers 164.

Because the data paths depicted in FIG. 17 are AC coupled, it is necessary to ensure that the data signaling scheme used for these data communications are DC balanced, i.e., that the data streams have little or no DC content. This can be achieved by using Manchester encoding of the data streams, or other data encoding such as 8B/10B as specified in the IEEE802.3z specification for Gigabit Ethernet. Other coding can be used in the alternative.

The foregoing description is provided for the purpose of explanation and is not to be construed as limiting. While the embodiments have been described with reference to specific embodiments or methods, it is understood that the words which have been used herein are words of description and illustration, rather than words of limitation. Furthermore, although particular embodiments and methods have been described herein, the appended claims are not intended to be limited to the particulars disclosed herein. Those skilled in the relevant art, having the benefit of the teachings of this specification, may effect numerous modifications to the embodiments and methods as described herein, and changes may be made without departing from the scope of the appended claims.

PARTS LIST system 10
base unit 12
probe 14
probe 14a
probe 14b
battery pack 16
battery 17
housing 18
enclosure 19 of battery pack 16
transducer array 20
first circuit board assembly 22
second circuit board assembly 24
electrical connector 25
printed wire board 26
electrical connectors 27
rigid standoff 29
upper clamshell 30
lower clamshell 32
nosepiece 34
battery panel 36
interior volume 37
acoustic window 38
teeth 39 (of nosepiece 34 and upper and lower clamshells 30, 32)
nosepiece subassembly 40
epoxy backfill 41
backshell 42
joints 44 (of upper and lower clamshells 30, 32)
bracket 48
rigid standoffs 50
lower clamshell 52
compliant standoffs 52
leads 54
contacts 56
bumpers 60
cladding 62
contacts 66
gasket 70
surface 72
projections 80
arms 82 of battery pack 16
end portions 84 of arms 82
inclined surfaces of projections 80
rounded portions 86 projections 80
indentations 88 of end portions 84
relay 92
switch 92a
hall effect sensor 93
battery isolation circuit 94
MOSFET 95
magnet 96
switch 100
contact 102
membrane 104
transmit receive switch 105
charging station 106 (of base unit 12)
transmit pulser 107
receive amplifier 108
transmit controller 109 circuit boards 110 (of circuit board assemblies 22, 24)
time varying gain control circuit 114
receive data processor 116
analog to digital converter 118
on/off switch 119
transceiver 122
transceiver 123
image processor 124
monitor 126
battery charging contacts 130
reed relay 131
diode 132
switch 133
ohm resistor 134
MOSFET 136
capacitor 137
battery pack 138
diode 139
ohm resistor 140
resistor 141
capacitor 142
op-amp 143
probe charging stand 144
probe charging stand electrical contacts 145
contact wiper 146
cable 147 of cable assembly 149
first connector 148
cable assembly 149
second connector 151
electrical contacts 156
electrical contacts 157
probe connector mating face 160
cable connector mating face 161
transformer 164
base unit power supply 165
ground wire 166 of cable 147
housing 167 (of connectors 48, 151)
coating 168
shield 170

What is claimed is:

1. An ultrasound system, comprising:
a base unit;
a cordless removable battery pack comprising a battery, a housing of the battery and electrical contacts on the housing;
a removable cable assembly; and
a probe in communication with the base unit, comprising:
a housing of the probe, the housing of the probe including a single mating surface configured to receive both of the cordless removable battery pack and a first electrical connector of the removable cable assembly at different times, wherein the same mating surface electrical contacts only couples either the cordless removable battery pack or the first electrical connector of the removable cable assembly to the probe at a time;
a transducer array positioned within the housing, wherein the transducer array emits acoustical energy and receives return reflections of the acoustical energy; and
a transmitter, within the housing of the probe, mounted on a circuit substrate and communicatively coupled to the transducer array, wherein the transmitter stimulates the transducer array to emit acoustical energy, and the transmitter is configured to receive power, via the mating surface electrical contacts, from either the cordless removable battery pack or the first electrical connector.

2. The system of claim 1, wherein the mating surface electrical contacts comprise two electrical contacts disposed either within or on the mating surface, and each of the cordless removable battery pack and the first electrical connector comprise two electrical contacts that are configured to mate with the respective two electrical contacts of the probe, and
wherein the removable cable assembly comprises a cable with at least two electrical conductors, and a second electrical connector,
wherein the first electrical connector is mechanically connected to a first end of the cable and the second electrical connector is mechanically connected to a second end of the cable,
wherein the ultrasound system further comprises an electrically-insulative barrier mounted to the probe housing or to the battery pack and the first electrical connector so that the barrier encircles the electrical contacts when the probe and either the battery pack or the first electrical connector are mated.

3. The system of claim 2, wherein the base unit receives and processes output signals from the probe, and the base unit is configured to receive the second electrical connector.

4. The system of claim 3, wherein the first and second electrical connectors are configured such that either the first or second electrical connector is operable to be removably connected with the housing.

5. The system of claim 2, wherein either the battery pack or the first electrical connector is drawn into a partially mated position in relation to the probe, wherein either the battery pack or the first electrical connector is partially mated to the probe;
wherein either the battery pack or the first electrical connector and the probe exert a compressive force on the barrier when either the battery pack or the first electrical connector is in the partially mated position; and
wherein the partially mated battery pack or first electrical connector backs away from the probe as the partially mated battery pack or first electrical connector moves from the partially mated position to a fully mated position in relation to the probe so that the compressive force decreases as either the battery pack or the first electrical connector moves from the partially mated position to the fully mated position.

6. The system of claim 2, wherein the barrier is a gasket.

7. The system of claim 2, wherein the probe further comprises a four electrical contacts, and the battery pack and the first electrical connector comprises a four electrical contacts that mate with the respective four electrical contacts of the probe when the probe and either the battery pack or the first electrical connector are mated.

8. The system of claim 7, further comprising a second and a third electrically-insulative barrier mounted on at least one of a surface of the probe or the battery pack and the first electrical connector, wherein the second and third electrically-insulative barriers encircle the respective two of the electrical contacts of the probe or the battery pack and the first electrical connector.

9. The system of claim 1, further comprising an extension mounted on either the probe or the removable battery pack and the first electrical connector, and a projection mounted on the other of the probe or the battery pack or the first electrical connector, wherein engagement of the extension and the projection holds either the removable battery pack or the first electrical connector in a fully mated position with the probe.

10. The system of claim 9, wherein the extension is an elongated arm.

11. The system of claim 1, further comprising an acoustic transmit timing device communicatively coupled to the transmitter, wherein the acoustic transmit timing device controls the timing of pulses of the acoustical energy.

12. The system of claim 11, further comprising a time-varying gain circuit communicatively coupled to the transducer array for compensating for attenuation of acoustical energy received by the transducer array, and an analog to digital converter communicatively coupled to the time-varying gain circuit.

13. The system of claim 11, further comprising a receive amplifier communicatively coupled to the transducer array, wherein the receive amplifier amplifies the output of the transducer array.

14. The system of claim 1, wherein the housing further comprises a first electrical contact and a second electrical contact disposed either within or on the mating surface, the first electrical contact configured to communicate with an electrical contact of the battery pack and the second electrical contact configured to communicate with an electrical contact of the first electrical connector.

15. The system of claim 14, wherein the disposition of the first electrical contact within or on the mating surface is such that the first electrical contact is at least partially covered by the first electrical connector when the first electrical connector is in removable connection with the mating surface.

16. The system of claim 14, wherein the disposition of the second electrical contact within or on the mating surface is such that the second electrical contact is at least partially covered by the battery when the battery is in removable connection with the mating surface.

17. The system of claim 1, wherein the housing further comprises a first electrical contact disposed either within or on the mating surface, the first electrical contact configured to communicate with a respective electrical contact of whichever of the battery pack or the first electrical connector that is in removable connection with the mating surface.

18. The system of claim 1, wherein at least one of the housing or the battery pack includes magnetic material.

19. The system of claim 1, wherein the first electrical connector includes magnetic material.

20. An ultrasound system, comprising:
a probe comprising a housing and a transducer array positioned within the housing, wherein the transducer array emits acoustical energy and receives return reflections of the acoustical energy,
the housing including a single mating surface and a first electrical contact, the first electrical contact disposed either within or on the mating surface,
a cableless battery pack capable of being removably connected to the probe housing at the mating surface, and configured to provide power to the probe through the first electrical contact, and
a cable assembly comprising a first electrical connector capable of being removably connected to the probe housing at the mating surface, and configured to provide power to the probe through the first electrical contact,
wherein the same mating surface first electrical contact only couples at one time either the cordless removable battery pack or the first electrical connector of the removable cable assembly to the probe.

21. The system of claim 20, wherein the mating surface further includes a second electrical contact disposed either within or on the mating surface, and
wherein the cable assembly further comprises a cable comprising two electrical conductors, and a second electrical connector,
wherein the first electrical connector is mechanically connected to a first end of the cable and the second electrical connector is mechanically connected to a second end of the cable,
wherein the system further includes an electrically-insulative barrier mounted to the probe or to the battery pack and the first electrical connector so that the barrier encircles the electrical contacts when the probe and either the battery pack or the first electrical connector are mated.

22. The system of claim 21, further comprising a base unit, wherein the base unit receives and processes output signals from the probe, and the base unit is configured to receive the second electrical connector.

23. The system of claim 22, wherein the first and second electrical connectors are configured such that either the first or second electrical connector is operable to be removably connected with the housing.

24. The system of claim 21, wherein either the cableless battery pack or the first electrical connector is drawn into a partially mated position in relation to the probe, wherein either the battery pack or the first electrical connector is partially mated to the probe;
either the battery pack or the first electrical connector and the probe exert a compressive force on the barrier when either the battery pack or the first electrical connector is in the partially mated position; and
wherein the partially mated battery pack or first electrical connector backs away from the probe as the partially mated battery pack or first electrical connector moves from the partially mated position to a fully mated position in relation to the probe so that the compressive force decreases as either the battery pack or the first electrical connector moves from the partially mated position to the fully mated position.

25. The system of claim 21, wherein the barrier is a gasket.

26. The system of claim 21, wherein the probe further comprises four electrical contacts, and the cableless battery pack and the first electrical connector comprises four electrical contacts that mate with the respective four electrical contacts of the probe when the probe and either the battery pack or the first electrical connector are mated.

27. The system of claim 26, further comprising a second and a third electrically-insulative barrier mounted on at least one of a surface of the probe or the cableless battery pack and the first electrical connector, wherein the second and third barriers encircle the respective two of the electrical contacts of the probe or the battery pack and the first electrical connector.

28. The system of claim 21, wherein at least one of the housing or the cableless battery pack includes magnetic material.

29. The system of claim 21, wherein the first electrical connector includes magnetic material.

30. The system of claim 20, wherein the probe further comprises a circuit substrate, and a transmitter mounted on the circuit substrate and communicatively coupled to the transducer array, wherein the transmitter stimulates the transducer array to emit acoustical energy.

31. The system of claim 30, further comprising an acoustic transmit timing device communicatively coupled to the transmitter, wherein the acoustic transmit timing device controls the timing of pulses of the acoustical energy.

32. The system of claim 31, further comprising a time-varying gain circuit communicatively coupled to the transducer array for compensating for attenuation of acoustical energy received by the transducer array, and an analog to digital converter communicatively coupled to the time-varying gain circuit.

33. The system of claim 31, further comprising a receive amplifier communicatively coupled to the transducer array, wherein the receive amplifier amplifies the output of the transducer array.

34. The system of claim 20, further comprising:
an extension mounted on one of the probe and either the cableless battery pack or the first electrical connector, and
a projection mounted on the other of the probe and either the cableless battery pack or the first electrical connector,
wherein engagement of the extension and the projection holds either the cableless battery pack or the first electrical connector in a fully mated position.

35. A method for performing an ultrasound procedure, comprising:
providing a probe comprising a housing and a transducer array positioned within the housing, wherein the transducer array emits acoustical energy and receives return reflections of the acoustical energy, the housing including at least a single mating surface and a first electrical contact, the first electrical contact disposed either within or on the mating surface, wherein the mating surface is configured to receive a cordless removable battery pack or a first electrical connector of a removable cable assembly, wherein the first electrical contact only couples at one time either the cordless removable battery pack or the first electrical connector of the removable cable assembly to the probe; and
providing a base unit that is configured to concurrently communicate power and information with the probe via the first electrical connector of the removable cable assembly when the first electrical connector is connected to the mating surface of the probe, and to concurrently communicate information with the probe wirelessly when the cordless removable battery pack is connected to the mating surface.

36. The method of claim 35, further comprising:
providing the removable cable assembly, wherein the removable cable assembly is sterile;
removably connecting the first connector of the cable assembly directly to the mating surface of the probe; and
removably connecting a second connector of the cable assembly to the base unit,
wherein the removably connecting the first connector of the cable assembly to the probe comprises creating an electrically-insulative barrier that encircles the first electrical contact on the probe and an electrical contact on the first connector of the cable assembly.

37. The method of claim 36, wherein the first connector of the cable assembly functions properly in the presence of electrically conductive fluids when mated with the probe.

38. The method of claim 36, wherein the removably connecting the first connector of the cable assembly to the probe further comprises drawing the first connector into a partially mated position in relation to the probe as the connector and the probe are partially mated to cause the connector and the probe to exert a first compressive force on the barrier; and causing the connector to move from the partially mated position to a fully mated position in which a compressive force exerted on the barrier is less than the first compressive force.

39. The method of claim 35, wherein the first and second connectors of the cable assembly are interchangeable.

40. The method of claim 35, wherein the sterile cable assembly is intended for a single use.

* * * * *